US006949362B2

(12) United States Patent
Bramucci et al.

(10) Patent No.: US 6,949,362 B2
(45) Date of Patent: Sep. 27, 2005

(54) RHODOCOCCUS CLONING AND EXPRESSION VECTORS

(75) Inventors: Michael G. Bramucci, Folsom, PA (US); Qiong Cheng, Wilmington, DE (US); Kristy N. Kostichka, Wilmington, DE (US); Jean-Francois Tomb, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 102 days.

(21) Appl. No.: 10/007,527

(22) Filed: Dec. 5, 2001

(65) Prior Publication Data

US 2003/0044807 A1 Mar. 6, 2003

Related U.S. Application Data

(60) Provisional application No. 60/254,868, filed on Dec. 12, 2000.

(51) Int. Cl.$^7$ .......................... C12P 21/06; C12N 1/20; C12N 15/00; C07H 21/02
(52) U.S. Cl. .............. 435/69.1; 435/320.1; 435/252.1; 435/252.3; 435/471; 536/23.1
(58) Field of Search .......................... 435/69.1, 320.1, 435/252.1, 471, 252.3; 536/23.1

(56) References Cited

U.S. PATENT DOCUMENTS

| | | | |
|---|---|---|---|
| 4,920,054 | A | 4/1990 | Kozlowski et al. |
| 4,952,500 | A | 8/1990 | Finnerty et al. |
| 5,246,857 | A | 9/1993 | Yu et al. |
| 5,705,386 | A | 1/1998 | Mizunashi et al. |
| 5,776,771 | A | 7/1998 | Yu et al. |

FOREIGN PATENT DOCUMENTS

| | | |
|---|---|---|
| EP | 704530 A2 | 4/1995 |
| JP | 07255484 | 10/1995 |
| JP | 08056669 | 3/1996 |
| JP | 10248578 | 9/1998 |
| WO | WO 89/07151 A1 | 8/1989 |

OTHER PUBLICATIONS

Kostichka et al. A small cryptic plasmid from *Rhodococcus erythropolis*: characterization and utility for gene expression. Appl. Microbiol. Biotechnol. 62(1):61–8, 2003.*

Fleischmann et al., Science 269 (5223), 496–512, 1995.
Iiyina, T. V. et al., Nucleic Acids Research, 20: 3279–3285.
Kendall, K. J. et al., J. Bacteriol. 170: 4634–4651, 1988.
Servin–Gonzalez, L. Plasmid. 30: 131–140, 1993.
Servin–Gonzalez, L. Microbiology, 141: 2499–2510, 1995.
Katoaka, M. et al.; Plasmid. 32: 55–69, 1994.
Khan, S. A., Microbiol. and Mol.Biology Reviews, 61: 442–455, 1977.
Suzuki, I. et al., FEMS Microbiol. Lett. 150: 283–288, 1997.
Dabbs, 1990, Plasmid 23: 242–247.
Dansen, G. H., GI:3212128.
Mendes, et al., GI:6523480.
Quan and Dabbs, 1993, Plasmid, 29: 74–79.
Warhurst and Fewson, 1994, Crit. Rev. Biotechnol., 14:29–73.
Finnerty, 1992, Annu. Rev. Microbiol., 46: 193–218.
Desomer et al., 1988, J. Bacteriol., 170: 2401–2405.
Desomer et al., 1990, Appl. Environ. Microbiol., 56: 2818–2815.
Dabbs et al., 1995, Biotekhnologiya, Development of Improved *Rhodococcus* Plasmid Vectors and Their Using in Cloning Genes of Potential Commercial and Medical Importance, pp. 117–123.
De Mot, et al., 1997, Microbiol., 143: 3137–3147.
Hashimoto et al., 1992, J. Gen. Microbiol., 138: 1003–1010.
Bigey et al., 1995, Gene, 154: 77–79.
Kulakov et al., 1997, plasmit, 38:61–69.
Zheng et al., 1997, Plasmid 38: 180–187.
Vogt Singer et al., 1988, J. Bacteriol., 170: 638–645.
Shao et al., 1995. Lett. Appl. Microbiol., 21: 261–266.
Duran, 1998, J. Basic Microbiol., 38: 101–106.
Denis–Larose et al., 1998, Appl. Environ. Microbiol., 64: 4363–4367.
Billington, et al., J. Bacteriol., 180 (12), 3233–3236, 1998.
Gilbert et al., "pBR328 cloning vector", Database accession No. L08858, XP002225297, Oct. 10, 1983.

* cited by examiner

Primary Examiner—Jeffrey Fredman
Assistant Examiner—Sumesh Kaushal

(57) ABSTRACT

A plasmid has been isolated from *Rhodococcus erythropolis* strain AN12 comprising a unique replication protein. The replication protein may be used in a variety of cloning and expression vectors and particularly in shuttle vectors for the expression of heterologous genes in *Rhodococcus* sp.

13 Claims, 4 Drawing Sheets

RHODOCOCCUS CLONING AND EXPRESSION VECTORS

This application claims the benefit of U.S. Provisional Application No. 60/254,868 filed Dec. 12, 2000.

FIELD OF THE INVENTION

The invention relates to the field of microbiology. More specifically, vectors are provided for the cloning and expression of genes in *Rhodococcus* species and like organisms.

BACKGROUND OF THE INVENTION

Gram-positive bacteria belonging to the genus *Rhodococcus*, some of which were formerly classified as *Nocardia, Mycobacterium, Gordona,* or *Jensenia* spp., or as members of the "rhodochrous" complex, are widely distributed in the environment. Members of the genus *Rhodococcus* exhibit a wide range of metabolic activities, including antibiotic and amino acid production, biosurfactant production, and biodegradation and biotransformation of a large variety of organic and xenobiotic compounds (see Vogt Singer and Finnerty, 1988, *J. Bacteriol.*, 170:638–645; Quan and Dabbs, 1993, *Plasmid*, 29: 74–79; Warhurst and Fewson, 1994, *Crit. Rev. Biotechnol.*, 14:29–73). Unfortunately, few appropriate genetic tools exist to investigate and exploit these metabolic activities in *Rhodococcus* and like organisms (see Finnerty, 1992, *Annu. Rev. Microbiol.*, 46:193–218).

Recently, several *Rhodococcus* plasmids and *Rhodococcus-Escherichia coli* shuttle vectors have been described. These plasmids and vectors can be divided into five different derivation groups:

a) plasmids derived from *Rhodococcus fascians* (Desomer et al., 1988, *J. Bacteriol.*, 170:2401–2405; and Desomer et al., 1990, *Appl. Environ. Microbiol.*, 56:2818–2815); b) plasmids derived from *Rhodococcus erythropolis* (JP 10248578; EP 757101; JP 09028379; U.S. Pat. No. 5,705, 386; Dabbs et al., 1990, *Plasmid*, 23:242–247; Quan and Dabbs, 1993, *Plasmid*, 29:74–79; Dabbs et al., 1995, *Biotekhnologiya*, 7–8:129–135; De Mot, et al., 1997, *Microbiol.*, 143:3137–3147); c) plasmids derived from *Rhodococcus rhodochrous* (EP 482426; U.S. Pat. No. 5,246,857; JP 1990-270377; JP 07255484; JP 08038184; U.S. Pat. No. 5,776,771; EP 704530; JP 08056669; Hashimoto et al., 1992, *J. Gen. Microbiol.*, 138:1003–1010; Bigey et al., 1995, *Gene*, 154:77–79; Kulakov et al., 1997, *Plasmid*, 38:61–69); d) plasmids derived from *Rhodococcus equi* (U.S. Pat. No. 4,920,054; Zheng et al., 1997, Plasmid, 38:180–187) and e) plasmids derived from a *Rhodococcus* sp. (WO 89/07151; U.S. Pat. No. 4,952,500; Vogt Singer et al., 1988, *J. Bacteriol.*, 170:638–645; Shao et al., 1995, *Lett. Appl. Microbiol.*, 21:261–266; Duran, 1998, *J. Basic Microbiol.*, 38:101–106; Denis-Larose et al., 1998, *Appl. Environ. Microbiol.*, 64:4363–4367).

While these prior studies describe several plasmids and shuttle vectors, the relative number of commercially available tools that exist for the genetic manipulation of *Rhodococcus* and like organisms remains limited. One of the difficulties in developing a suitable expression vector for *Rhodococcus* is the limited number of sequences encoding replicase or replication proteins (rep) which allow for plasmid replication in this host. Knowledge of such sequences is needed to design a useful expression or shuttle vector. Although replication sequences are known for other shuttle vectors that function in *Rhodococcus* (see for example Denis-Larose et al., 1998, *Appl. Environ. Microbiol.*, 64:4363–4367); Billington, et al., *J. Bacteriol.* 180 (12), 3233–3236 (1998); Dasen, G. H. GI:3212128; and Mendes, et al, GI:6523480) they are rare.

Similarly, another concern in the design of shuttle expression and shuttle vectors in *Rhodococcus* is plasmid stability. The stability of any plasmid is often variably and maintaining plasmid stability in a particular host usually requires the antibiotic selection, which is neither an economical nor a safe practice in the industrial scale production. Little is known about genes or proteins that function to increase or maintain plasmid stability without antibiotic selection.

The problem to be solved, therefore is to provide additional useful plasmid and shuttle vectors for use in genetically engineering *Rhodococcus* and like organisms. Such a vector will need to have a robust replication protein and must be able to be stably maintained in the host.

Applicants have solved the stated problem by isolating and characterizing a novel cryptic plasmid, pAN12, from *Rhodococcus erythropolis* strain AN12 and constructing a novel *Escherichia coli-Rhodococcus* shuttle vector using pAN12. Applicants' invention provides important tools for use in genetically engineering *Rhodococcus* species (sp.) and like organisms. The instant vectors contain a replication sequence that is required for replication of the plasmid and may be used to isolate or design other suitable replication sequences for plasmid replication. Additionally, the instant plasmids contain a sequence having homology to a cell division protein which is required for plasmid stability. Applicants' shuttle vectors are particularly desirable because they are able to coexist with other shuttle vectors in the same *Rhodococcus* host cell. Therefore, Applicants' vectors may also be used in combination with other compatible plasmids for co-expression in a single host cell.

SUMMARY OF THE INVENTION

The present invention provides novel nucleic acids and vectors comprising these nucleic acids for the cloning and expression of foreign genes in *Rhodococcus* sp. In particular, the present invention provides a novel plasmid isolated from a proprietary strain AN12 of *Rhodococcus erythropolis* and a novel shuttle vector prepared from this plasmid that can be replicated in both *Escherichia coli* and members of the *Rhodococcus* genus. These novel vectors can be used to clone and genetically engineer a host bacterial cell to express a polypeptide of protein of interest. In addition, Applicants have identified and isolated several unique coding regions on the plasmid that have general utility for plasmid replication and stability. The first of these is a nucleic acid encoding a unique replication protein, rep, within the novel plasmid. The second sequence encodes a protein having significant homology to a cell division protein and has been determined to play a role in maintaining plasmid stability. Both the replication protein and the stability protein nucleotide sequences may be used in a variety of cloning and expression vectors and particularly in shuttle vectors for the expression of homologous and heterologous genes in *Rhodococcus* sp. and like organisms.

Thus, the present invention relates to an isolated nucleic acid molecule encoding a replication protein selected from the group consisting of: (a) an isolated nucleic acid encoding the amino acid sequence as set forth in SEQ ID NO:2; (b) an isolated nucleic acid that hybridizes with (a) under the following hybridization conditions: 0.1×SSC, 0.1% SDS, 65° C. and washed with 2×SSC, 0.1% SDS followed by 0.1×SSC, 0.1% SDS; or an isolated nucleic acid that is complementary to (a), or (b).

Similarly the present invention provides an isolated nucleic acid molecule encoding a plasmid stability protein selected from the group consisting of: (a) an isolated nucleic acid encoding the amino acid sequence as set forth in SEQ ID NO:4; (b) an isolated nucleic acid that hybridizes with (a) under the following hybridization conditions: 0.1×SSC, 0.1% SDS, 65° C. and washed with 2×SSC, 0.1% SDS followed by 0.1×SSC, 0.1% SDS; or an isolated nucleic acid that is complementary to (a) or (b).

The invention additionally provides polypeptides encoded by the present nucleotide sequences and transformed hosts containing the same.

Methods for the isolation of homologs of the present genes are also provided. In one embodiment the invention provides a method of obtaining a nucleic acid molecule encoding an replication protein or stability protein comprising: (a) probing a genomic library with a nucleic acid molecule of the present invention; (b) identifying a DNA clone that hybridizes with the nucleic acid molecule of the present invention; and (c) sequencing the genomic fragment that comprises the clone identified in step (b), wherein the sequenced genomic fragment encodes a replication protein or a stability protein.

In another embodiment the invention provides a method of obtaining a nucleic acid molecule encoding a replication protein or a stability protein comprising: (a) synthesizing at least one oligonucleotide primer corresponding to a portion of the sequences of the present invention; and (b) amplifying an insert present in a cloning vector using the oligonucleotide primer of step (a);
wherein the amplified insert encodes a portion of an amino acid sequence encoding a replication protein or a stability protein.

In a preferred embodiment the invention provides plasmids comprising the genes encoding the present replication and stability proteins and optionally selectable markers. Preferred hosts for plasmid replication for gene expression are the Actinomycetales bacterial family and specifically the *Rhodococcus* genus.

In another preferred embodiment the invention provides a method for the expression of a nucleic acid in an Actinomycetales bacteria comprising: a) providing a plasmid comprising: (i) the nucleic acids of the present invention encoding the rep and stability proteins; (ii) at least one nucleic acid encoding a selectable marker; and (iii) at least one promoter operably linked to a nucleic acid fragment to be expressed; b) transforming an Actinomycetales bacteria with the plasmid of (a); and
c) culturing the transformed Actinomycetales bacteria of (b) for a length of time and under conditions whereby the nucleic acid fragment is expressed.

In an alternate embodiment the invention provides a method for the expression of a nucleic acid in an Actinomycetales bacteria comprising:
a) providing a first plasmid comprising: (i) the nucleic acid of the present invention encoding a rep protein; (ii) at least one nucleic acid encoding a selectable marker; and (iii) at least one promoter operably linked to a nucleic acid fragment to be expressed; b) providing at least one other plasmid in a different incompatibility group as the first plasmid, wherein the at least one other plasmid comprises: (ii) at least one nucleic acid encoding a selectable marker; and (iii) at least one promoter operably linked to a nucleic acid fragment to be expressed; c) transforming an Actinomycetales bacteria with the plasmids of (a) and (b); and d) culturing the transformed Actinomycetales bacteria of (c) for a length of time and under conditions whereby the nucleic acid fragment is expressed.

SEQUENCE DESCRIPTIONS

Figure 1:
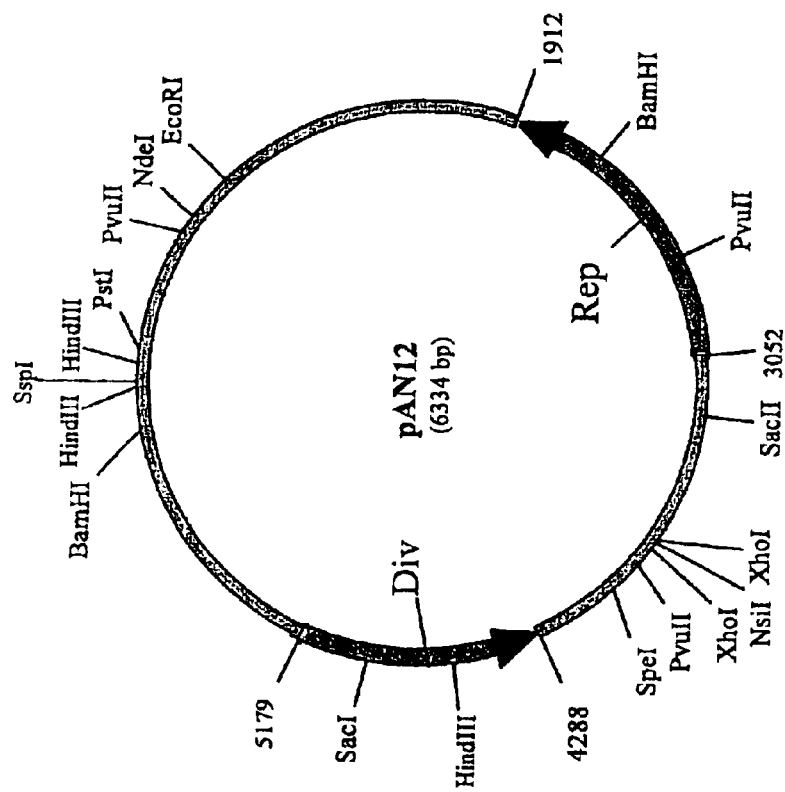
FIG. 1 is a restriction endonuclease map of pAN12, a cryptic plasmid from *Rhodococcus erythropolis* strain AN12.

The invention can be more fully understood from the following detailed description and the accompanying sequence descriptions which form a part of this application.

Applicant(s) have provided 30 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

| Description | SEQ ID Nucleic acid | SEQ ID Peptide |
| --- | --- | --- |
| Replications (Rep) protein isolated from *Rhodococcus* AN12 | 1 | 2 |
| Plasmid stability protein isolated from *Rhodococcus* AN12 | 3 | 4 |
| plasmid pAN12 | 5 | |
| Plasmid pRHBR17 | 6 | |
| Plasmid pRHBR171 | 7 | |
| pAN12 origin of replication | 8 | |
| HK12 primer | 9 | |
| HK13 primer | 10 | |
| HK14 primer | 11 | |
| 16S rRNA from *Rhodococcus* AN12 | 12 | |
| M13 universal primer | 13 | |
| M13 reverse primer | 14 | |
| 1.7 kb(1) Fragment | 15 | |
| 1.7 (kb)2 Fragment | 16 | |
| 4.4 kb Fragment | 17 | |
| the Primer N | 18 | |
| rep1 primer | 19 | |
| rep2 primer | 20 | |
| *Arcanobacterium pyrogenes* replication protein | | 21 |
| *Streptomyces lividans* replication protein | | 22 |
| *Streptomyces phaeochromogenes* replication protein | | 23 |
| *Streptomyces nigrifaciens* replication protein | | 24 |
| *Streptomyces lividans* Ori sequence | 25 | |
| *Streptomyces phaeochromogenes* Ori sequence | 26 | |

-continued

| Description | SEQ ID Nucleic acid | SEQ ID Peptide |
|---|---|---|
| *Streptomyces nigrifaciens* Ori sequence | 27 | |

DETAILED DESCRIPTION OF THE INVENTION

Applicants have isolated and characterized a novel cryptic plasmid, pAN12, from *Rhodococcus erythropolis* strain AN12 and constructed a novel *Escherichia coli-Rhodococcus* shuttle vector using pAN12. Applicants' invention provides important tools for use in genetically engineering *Rhodococcus* species and like organisms. In addition, Applicants have identified and isolated a nucleic acid encoding a unique replication protein, rep, from the novel plasmid. This replication protein encoding nucleic acid may be used in a variety of cloning and expression vectors and particularly in shuttle vectors for the expression of homologous and heterologous genes in *Rhodococcus* species (sp.) and like organisms. Similarly, Applicants have identified and characterized a sequence on the plasmid encoding a protein useful for maintaining plasmid stability. Applicants' shuttle vectors are particularly desirable because they are able to coexist with other shuttle vectors in the same *Rhodococcus* host cell. Therefore, Applicants' vectors may also be used in combination with other compatible plasmids for co-expression in a single host cell.

In another embodiment the invention provides a compact shuttle vector that has the ability to replicate both in *Rhodococcus* and *E. coli*, yet is small enough to transport large DNA.

In this disclosure, a number of terms and abbreviations are used. The following definitions are provided and should be helpful in understanding the scope and practice of the present invention.

In a specific embodiment, the term "about" or "approximately" means within 20%, preferably within 10%, and more preferably within 5% of a given value or range.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Another set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Maniatis, supra, 9.50–9.51). For hybridizations with shorter nucleic acids, i.e., oligonucleotides, the position of mismatches becomes more important, and the length of the oligonucleotide determines its specificity (see Maniatis, supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "probe" refers to a single-stranded nucleic acid molecule that can base pair with a complementary single stranded target nucleic acid to form a double-stranded molecule.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, the term "oligonucleotide" refers to a nucleic acid, generally of about 18 nucleotides, that is hybridizable to a genomic DNA molecule, a cDNA molecule, or an mRNA molecule. Oligonucleotides can be labeled, e.g., with $^{32}$P-nucleotides or nucleotides to which a label, such as biotin, has been covalently conjugated. An oligonucleotide can be used as a probe to detect the presence of a nucleic acid according to the invention. Similarly, oligonucleotides (one or both of which may be labeled) can be used as PCR primers, either for cloning full length or a fragment of a nucleic acid of the invention, or to detect the presence of nucleic acids according to the invention. In a further embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA "coding sequence" is a double-stranded DNA sequence which is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

The terms "restriction endonuclease" and "restriction enzyme" refer to an enzyme which binds and cuts within a specific nucleotide sequence within double stranded DNA.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin which are responsible for expressing different proteins or even synthetic proteins (a heterologous region). In particular, the sequences can be sequences of prokaryotic, eukaryotic, or viral genes or derived sequences which stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"Heterologous" DNA refers to DNA not naturally located in the cell, or in a chromosomal site of the cell. Preferably, the heterologous DNA includes a gene foreign to the cell.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

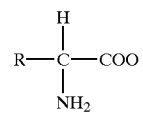

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "homologous" in all its grammatical forms and spelling variations refers to the relationship between proteins that possess a "common evolutionary origin," including proteins from superfamilies and homologous proteins from different species (Reeck et al., 1987, Cell 50:667). Such proteins (and their encoding genes) have sequence homology, as reflected by their high degree of sequence similarity.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

A "vector" is any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. Viral vectors include retrovirus, adeno-associated virus, pox, baculovirus, vaccinia, herpes simplex, Epstein-Barr and adenovirus vectors. Non-viral vectors include plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of DNA that replicates sequentially and which comprises an origin of replication, such as a plasmid, phage or cosmid, to which another DNA segment may be attached so as to bring about the replication of the attached segment. Cloning vectors may be capable of replication in one cell type, and expression in another ("shuttle vector").

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase.

The term "rep" or "repA" refers to a replication protein which controls the ability of a *Rhodococcus* plasmid to replicate. As used herein the rep protein will also be referred to as a "replication protein" or a "replicase". The term "rep" will be used to delineate the gene encoding the rep protein.

The term "div" refers to a protein necessary for maintaining plasmid stability. The div protein has significant homology to cell division proteins and will also be referred to herein as a "plasmid stability protein".

The terms "origin or replication" or "ORI" mean a specific site or sequence within a DNA molecule at which DNA replication is initiated. Bacterial and phage chromosomes have a single origin of replication.

The term "pAN12" refers to a plasmid comprising all or a substantial portion of the nucleotide sequence as set forth in SEQ ID NO:5, wherein the plasmid comprises a rep encoding nucleic acid comprising a nucleotide sequence as set forth in SEQ ID NO:1, a div encoding nucleic acid comprising a nucleotide sequence as set forth in SEQ ID NO:3, and an origin of replication comprising a nucleotide sequence as set forth in SEQ ID NO:8.

The term "pRHBR17" refers to an *Escherichia coli-Rhodococcus* shuttle vector comprising all or a substantial portion of the nucleotide sequence as set forth in SEQ ID NO:6, wherein the shuttle vector comprises a rep encoding nucleic acid comprising a nucleotide sequence as set forth in SEQ ID NO:1, a div encoding nucleic acid comprising a nucleotide sequence as set forth in SEQ ID NO:3, and an origin of replication comprising a nucleotide sequence as set forth in SEQ ID NO:8.

The term "pRHBR171" refers to an *Escherichia coli-Rhodococcus* shuttle vector comprising all or a substantial portion of the nucleotide sequence as set forth in SEQ ID NO:7, wherein the shuttle vector comprises a rep encoding nucleic acid comprising a nucleotide sequence as set forth in SEQ ID NO:1, a div encoding nucleic acid comprising a nucleotide sequence as set forth in SEQ ID NO:3, and an origin of replication comprising a nucleotide sequence as set forth in SEQ ID NO:8.

The term "genetic region" will refer to a region of a nucleic acid molecule or a nucleotide sequence that comprises a gene encoding a polypeptide.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

The term "incompatibility" as applied to plasmids refers to the inability of any two plasmids to co-exist in the same cell. Any two plasmids fom the same incompatibility group can not be maintained in the same cell. Plasmids from different "incompatibility groups" can be in the same cell at the same time. Incompatibility groups are most extensively worked out for conjugative plasmids in the gram negative bacteria.

The term "Actinomycetales bacterial family" will mean a bacterial family comprised of genera, including but not limited to *Actinomyces, Actinoplanes, Arcanobacterium, Corynebacterium, Dietzia, Gordonia, Mycobacterium, Nocardia, Rhodococcus, Tsukamurella, Brevibacterium, Arthrobacter, Propionibacterium, Streptomyces, Micrococcus,* and *Micromonospora.*

Nucleic Acids of the Invention

Applicants have identified and isolated a nucleic acid encoding a unique replication protein, rep, within a novel *Rhodococcus* plasmid of the invention. This replication protein encoding nucleic acid may be used in a variety of cloning and expression vectors and particularly in shuttle vectors for the expression of homologous and heterologous genes in *Rhodococcus* sp. and like organisms. Comparisons of the nucleotide and amino acid sequences of the present replication protein indicated that the sequence was unique, having only 51% identity and a 35% similarity to the 459 amino acid Rep protein from *Arcanobacterium pyogenes* (Billington, S. J. et al, *J. Bacteriol*. 180, 3233–3236,1998) as aligned via the Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.).

Applicants have identified and isolated a nucleic acid encoding a unique plasmid stability protein having homology to a putative cell division (div) protein within a novel *Rhodococcus* plasmid of the invention. The stability protein is unique when compared with sequences in the public database having only 24% identity and a 40% similarity to the C-terminal portion of the 529 amino acid putative cell division protein from *Haemophilus influenzae* (Fleischmann et al., *Science* 269 (5223), 496–512 (1995).

Thus a sequence is within the scope of the invention if it encodes a replication function and comprises a nucleotide sequence encoding a polypeptide of at least 379 amino acids that has at least 70% identity based on the Smith-Waterman method of alignment (W. R. Pearson, supra) when compared to a polypeptide having the sequence as set forth in SEQ ID NO:2, or a second nucleotide sequence comprising the complement of the first nucleotide sequence.

Similarly a sequence is within the scope of the invention if it encodes a stability function and comprises a nucleotide sequence encoding a polypeptide of at least 296 amino acids that has at least 70% identity based on the Smith-Waterman method of alignment (W. R. Pearson, supra) when compared to a polypeptide having the sequence as set forth in SEQ ID NO:4, or a second nucleotide sequence comprising the complement of the first nucleotide sequence.

Accordingly, preferred amino acid fragments are at least about 70%–80% identical to the sequences herein. Most preferred are amino acid fragments that are at least 90–95% identical to the amino acid fragments reported herein. Similarly, preferred encoding nucleic acid sequences corresponding to the instant rep and div genes are those encoding active proteins and which are at least 70% identical to the nucleic acid sequences of reported herein. More preferred rep or div nucleic acid fragments are at least 80% identical to the sequences herein. Most preferred are rep and div nucleic acid fragments that are at least 90–95% identical to the nucleic acid fragments reported herein.

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies [e.g., polymerase chain reaction, Mullis et al., U.S. Pat. No. 4,683,202; ligase chain reaction (LCR), Tabor, S. et al., *Proc. Acad. Sci.* USA 82, 1074, (1985)] or strand displacement amplification [SDA, Walker, et al., *Proc. Natl. Acad. Sci. U.S.A.*, 89, 392, (1992)].

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis, supra 1989). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.).

Generally two short segments of the instant sequences may be used in polymerase chain reaction (PCR) protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol [Frohman et al., *PNAS USA* 85:8998 (1988)] to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated [Ohara et al., *PNAS USA* 86:5673 (1989); Loh et al., *Science* 243:217 (1989)].

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined and have been described above. Typically, the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Plasmids and Vectors of the Invention

Plasmids useful for gene expression in bacteria may be either self-replicating (autonomously replicating) plasmids or chromosomally integrated. The self-replicating plasmids have the advantage of having multiple copies of genes of interest, and therefore the expression level can be very high. Chromosome integration plasmids are integrated into the genome by recombination. They have the advantage of being stable, but they may suffer from a lower level of expression. In a preferred embodiment, plasmids or vectors according to the present invention are self-replicating and are used according to the methods of the invention.

Vectors or plasmids useful for the transformation of suitable host cells are well known in the art. Typically the vector or plasmid contains sequences directing transcription and translation of the relevant gene, a selectable marker, and sequences allowing autonomous replication or chromosomal integration. In a specific embodiment, the plasmid or vector comprises a nucleic acid according to the present invention. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Vectors of the present invention will additionally contain a unique replication protein (rep) as described above that facilitates the replication of the vector in the *Rhodococcus* host. Additionally the present vectors will comprise a stability coding sequence that is useful for maintaining the stability of the vector in the host and has a significant degree of homology to putative cell division proteins. The vectors of the present invention will contain convenient restriction sites for the facile insertion of genes of interest to be expressed in the *Rhodococcus* host.

The present invention relates to two specific plasmids, pAN12, isolated from a *Rhodococcus erythropolis* host and shuttle vectors derived and constructed therefrom. The pAN12 vector contains a unique Ori and replication and stability sequences for *Rhodococcus* while the shuttle vectors additionally contain an origin of replication (ORI) for replication in *E. coli* and antibiotic resistance markers for selection in *Rhodococcus* and *E. coli*.

Bacterial plasmids typically range in size from about 1 kb to about 200 kb and are generally autonomously replicating genetic units in the bacterial host. When a bacterial host has been identified that may contain a plasmid containing desirable genes, cultures of host cells are growth up, lysed and the plasmid purified from the cellular material. If the plasmid is of the high copy number variety, it is possible to purify it without additional amplification. If additional plasmid DNA is needed, a bacterial cell may be grown in the presence of a protein synthesis inhibitor such as chloramphenical which inhibits host cell protein synthesis and allow additional copies of the plasmid to be made. Cell lysis may be accomplished either enzymatically (i.e lysozyme) in the presence of a mild detergent, by boiling or treatment with strong base. The method chosen will depend on a number of factors including the characteristics of the host bacteria and the size of the plasmid to be isolated.

After lysis the plasmid DNA may be purified by gradient centrifugation (CsCl-ethidium bromide for example) or by phenol:chloroform solvent extraction. Additionally, size or ion exchange chromatography may be used as well as differential separation with polyethylene glycol.

Once the plasmid DNA has been purified, the plasmid may be analyzed by restriction enzyme analysis and sequenced to determine the sequence of the genes contained on the plasmid and the position of each restriction site to create a plasmid restriction map. Methods of constructing or isolating vectors are common and well known in the art (see for example Manitas supra, Chapter 1; Rohde, C., *World J. Microbiol. Biotechnol.* (1995), 11(3), 367–9); Trevors, J. T., *J. Microbiol. Methods* (1985), 3(5–6), 259–71).

Using these general methods the 6.3 kb pAN12 was isolated from *Rhodococcus erythropolis* AN12, purified and mapped (see FIG. 1) and the position of restriction sites determined (see Table 1, below).

TABLE 1

Restriction Endonuclease Cleavage of pAN12 (SEQ ID NO:5)

| Restriction Enzyme | Number/Nucleotide Location of Cleavage Site(s) | Size of Digested Fragments (kb) |
|---|---|---|
| Afl III | 1/515 | 6.334 |
| BamH I | 2/2240, 6151 | 2.423, 3.911 |
| Ban I | 1/4440 | 6.334 |
| Ban II | 1/4924 | 6.334 |
| Bbe I | 1/4440 | 6.334 |
| Bsm I | 1/6295 | 6.334 |
| BssH II | 1/2582 | 6.334 |
| Bsu36 I | 1/6070 | 6.334 |
| EcoR I | 1/797 | 6.334 |
| Esp I | 1/1897 | 6.334 |
| Hind III | 3/61, 4611, 6308 | 0.087, 1.697, 4.550 |
| Mlu I | 1/515 | 6.334 |
| Nar I | 1/4440 | 6.334 |
| Nde I | 1/626 | 6.334 |
| Nsi I | 1/3758 | 6.334 |
| PpuM I | 1/3060 | 6.334 |
| Pst I | 1/110 | 6.334 |
| Pvu II | 3/555, 2697, 3865 | 1.168, 2.142, 3.024 |
| Rsr II | 1/2866 | 6.334 |
| Sac I | 1/4924 | 6.334 |
| Sac II | 1/3272 | 6.334 |
| SnaB I | 1/2418 | 6.334 |
| Spe I | 1/3987 | 6.334 |
| Ssp I | 1/1 | 6.334 |
| StuI | 2/193, 2843 | 2.650, 3.684 |
| Tth111 I | 1/4900 | 6.334 |
| Xho I | 2/3746, 3784 | 0.038, 6.296 |

Once mapped, isolated plasmids may be modified in a number of ways. Using the existing restriction sites specific genes desired for expression in the host cell may be inserted within the plasmid. Additionally, using techniques well known in the art, new or different restriction sites may be engineered into the plasmid to facilitate gene insertion. Many native bacterial plasmid contain genes encoding resistance or sensitivity to various antibiotics. However, it may be useful to insert additional selectable markers to replace the existing ones with others. Selectable markers useful in the present invention include, but are not limited to genes conferring antibiotic resistance or sensitivity, genes encoding a selectable label such as a color (e.g. lac) or light (e.g. Luc; Lux) or genes encoding proteins that confer a particular phenotypic metabolic or morphological trait. Generally, markers that are selectable in both gram negative and gram positive hosts are preferred. Particularly suitable in the present invention are markers that encode antibiotic resistance or sensitivity, including but not limited to ampicillin resistance gene, tetracycline resistance gene, chloramphenicol resistance gene, kanamycin resistance gene, and thiostrepton resistance gene.

Plasmids of the present invention will contain a gene of interest to be expressed in the host. The genes to be expressed may be either native or endogenous to the host or foreign or heterologus genes. Particularly suitable are genes encoding enzymes involved in various synthesis or degradation pathways.

Endogenous genes of interest for expression in a *Rhodococcus* using Applicants' vectors and methods include, but are not limited to:
a) genes encoding enzymes involved in the production of isoprenoid molecules, for example, 1-deoxyxylulose-5-phosphate synthase gene (dxs) can be expressed in *Rhodococcus* to exploit the high flux for the isoprenoid pathway in this organism; b) genes encoding polyhydroxyalkanoic acid (PHA) synthases (phaC) which can also be expressed for the production of biodegradable plastics; c) genes encoding carotenoid pathway genes (eg, crtI) can be expressed to increase pigment production in *Rhodococcus*; d) genes encoding nitrile hydratases for production of acrylamide in *Rhodococcus* and the like, and d) genes encoding monooxygenases derived from waste stream bacteria.

Heterologous genes of interest for expression in a *Rhodococcus* include, but are not limited to: a) ethylene forming enzyme (efe) from *Pseudomonas syringae* for ethylene production, b) pyruvate decarboxylase (pdc), alcohol dehydrogenase (adh) for alcohol production, c) terpene synthases from plants for production of terpenes in *Rhodococcus*, d) cholesterol oxidase (choD) from *Mycobacterium tuberculosis* for production of the enzyme in *Rhodococcus*; and the like, and e) genes encoding monooxygenases derived from waste stream bacteria.

The plasmids or vectors according to the invention may further comprise at least one promoter suitable for driving expression of a gene in *Rhodococcus*. Typically these promoters including the initiation control regions will be derived from a *Rhodococcus* sp. Termination control regions may also be derived from various genes native to the preferred hosts. Optionally, a termination site may be unnecessary, however, it is most preferred if included.

Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (see for example EP 546049; WO 9324631). The secretion signal DNA or facilitator may be located between the expression-controlling DNA and the instant gene or gene fragment, and in the same reading frame with the latter.

The present invention also relates to a plasmid or vector that is able to replicate or "shuttle" between at least two different organisms. Shuttle vectors are useful for carrying genetic material from one organism to another. The shuttle vector is distinguished from other vectors by its ability to replicate in more than one host. This is facilitated by the presence of an origin of replication corresponding to each host in which it must replicate. The present vectors are designed to replicate in *Rhodococcus* for the purpose of gene expression. As such each contain a unique origin of replication for replication in *Rhodococcus*. This sequence is set forth in SEQ ID NO:8. Many of the genetic manipulations for this vector may be easily accomplished in *E. coli*. It is therefore particularly useful to have a shuttle vector comprising an origin of replication that will function in *E. coli* and other gram positive bacteria. A number of ORI sequences for gram positive bacteria have been determined and the sequence for the ORI in *E. coli* determined (see for example Hirota et al., Prog. *Nucleic Acid Res. Mol. Biol.* (1981), 26, 33–48); Zyskind, J. W.; Smith, D. W., *Proc. Natl. Acad. Sci. U.S.A.*, 77, 2460–2464 (1980), GenBank ACC. NO. (GBN): J01808). Preferred for use in the present invention are those ORI sequences isolated from gram positive bacteria, and particularly those members of the Actinomycetales bacterial family. Members of the Actinomycetales bacterial family include for example, the genera *Actinomyces, Actinoplanes, Arcanobacterium,* *Corynebacterium, Dietzia, Gordonia, Mycobacterium, Nocardia, Rhodococcus, Tsukamurella, Brevibacterium, Arthrobacter, Propionibacterium, Streptomyces, Micrococcus,* and *Micromonospora*.

Figure 2:
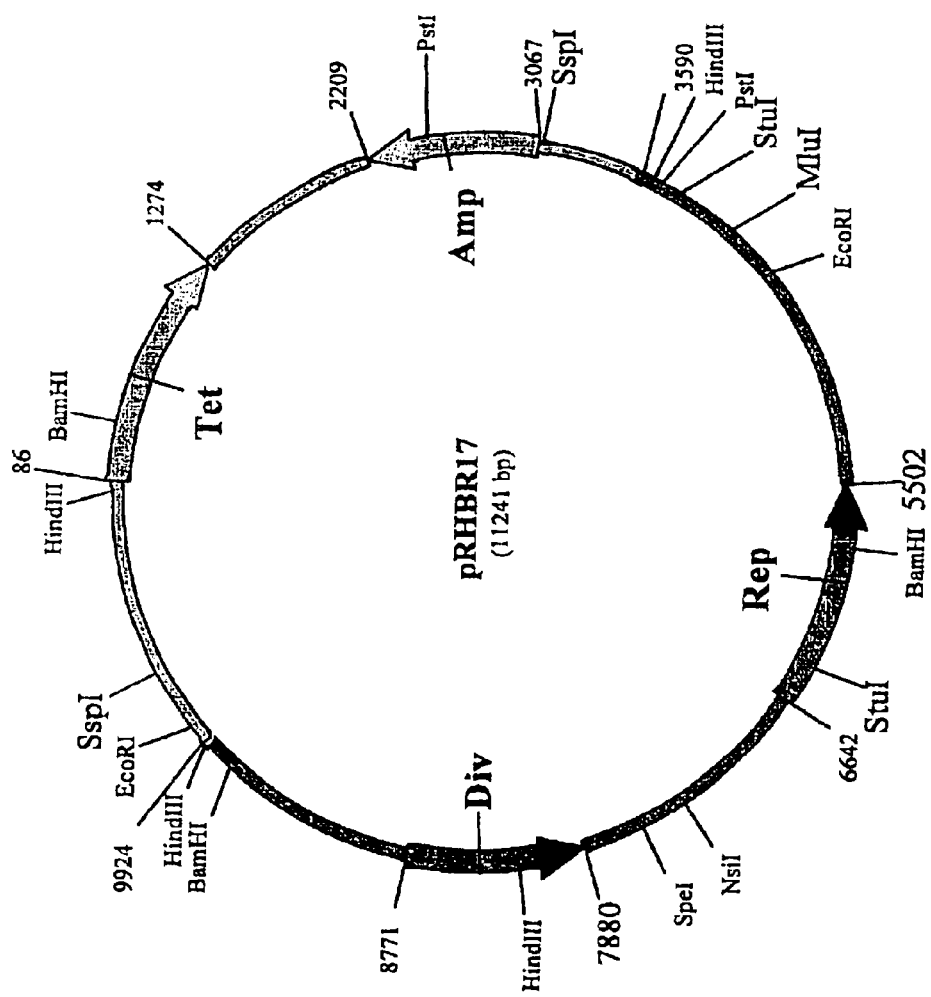
FIG. 2 is a restriction endonuclease map of pRhBR17, an *Escherichia coli-Rhodococcus* shuttle vector.

Two shuttle vectors are described herein, pRhBR17 and pRhBR171, each constructed and isolated separately but having the same essential features. The complete sequence of pRhBR17 is given in SEQ ID NO:6 and the complete sequence of the pRhBR171 is given in SEQ ID NO:7.

pRhBR17 has a size of about 11.2 kb and the characteristics of cleavage with restriction enzymes as shown in Table 2 and FIG. 2.

TABLE 2

Restriction Endonuclease Cleavage of pRhBR17 (SEQ ID NO:6)

| Restriction Enzyme | Number/Nucleotide Location of Cleavage Site(s) | Size of Digested Fragments (kb) |
|---|---|---|
| Afl III | 1/4105 | 11.241 |
| Ase I | 1/2450 | 11.241 |
| Bal I | 1/10289 | 11.241 |
| BamH I | 3/375, 5830, 9741 | 1.875, 3.911, 5.455 |
| BssH II | 1/6172 | 11.241 |
| EcoR I | 2/4387, 10024 | 5.604, 5.637 |
| EcoR V | 1/185 | 11.241 |
| Esp I | 1/5487 | 11.241 |
| Hind III | 4/29, 3651, 8201, 9898 | 1.372, 1.697, 3.622, 4.550 |
| Mlu I | 1/4105 | 11.241 |
| Nco I | 1/10325 | 11.241 |
| Nde I | 1/4216 | 11.241 |
| Nhe I | 1/229 | 11.241 |
| Nsi I | 1/7348 | 11.241 |
| PpuM I | 1/6650 | 11.241 |
| Pst I | 2/2520, 3700 | 1.180, 11.061 |
| Pvu II | 3/4145, 6287, 7455 | 1.168, 2.142, 7.931 |
| Rsr II | 1/6456 | 11.241 |
| Sac I | 1/8514 | 11.241 |
| Sac II | 1/6862 | 11.241 |
| SnaB I | 1/6008 | 11.241 |
| Spe I | 1/7577 | 11.241 |
| Ssp I | 2/3081, 10334 | 3.988, 7.253 |
| StuI | 2/3783, 6433 | 2.650, 8.591 |

Figure 3:
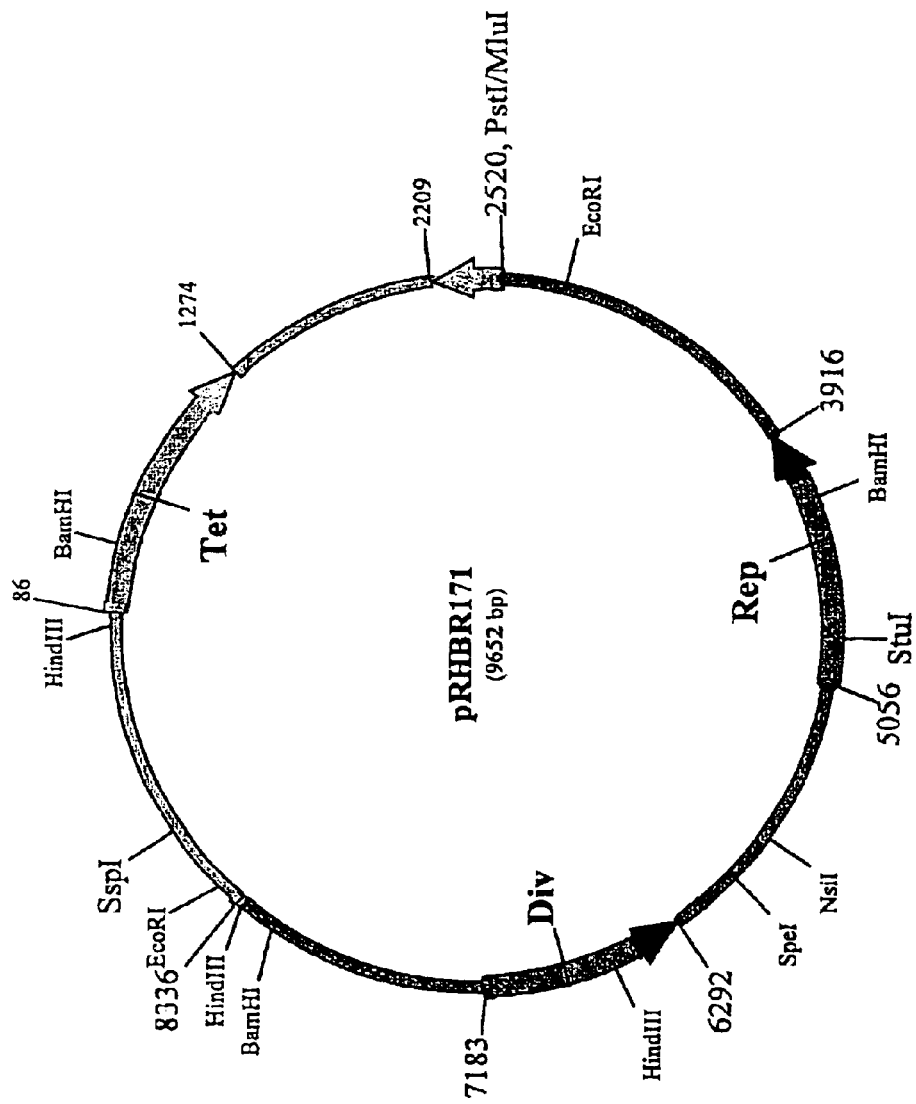
FIG. 3 is a restriction endonuclease map of pRhBR171, an *Escherichia coli-Rhodococcus* shuttle vector.

PRhBR171 has a size of about 9.7 kb and the characteristics of cleavage with restriction enzymes as shown in Table 3 and FIG. 3.

TABLE 3

Restriction Endonuclease Cleavage of pRhBR171 (SEQ ID NO:7)

| Restriction Enzyme | Number/Nucleotide Location of Cleavage Site(s) | Size of Digested Fragments (kb) |
|---|---|---|
| Ase I | 1/2450 | 9.652 |
| Bal I | 1/8700 | 9.652 |
| BamH I | 3/375, 4241, 8152 | 1.875, 3.866, 3.911 |
| BssH II | 1/4583 | 9.652 |
| EcoR I | 2/2798, 8435 | 4.015, 5.637 |
| EcoR V | 1/185 | 9.652 |
| Esp I | 1/3898 | 9.652 |
| Hind III | 3/29, 6612, 8309 | 1.372, 1.697, 6.583 |
| Nco I | 1/8736 | 9.652 |
| Nde I | 1/2627 | 9.652 |
| Nhe I | 1/229 | 9.652 |
| Nsi I | 1/5759 | 9.652 |
| PpuM I | 1/5061 | 9.652 |
| Pvu II | 3/2556, 4698, 5866 | 1.168, 2.142, 6.342 |
| Rsr II | 1/4867 | 9.652 |
| Sac I | 1/6925 | 9.652 |
| Sac II | 1/5273 | 9.652 |
| SnaB I | 1/4419 | 9.652 |

TABLE 3-continued

Restriction Endonuclease Cleavage of pRhBR171
(SEQ ID NO:7)

| Restriction Enzyme | Number/Nucleotide Location of Cleavage Site(s) | Size of Digested Fragments (kb) |
|---|---|---|
| Spe I | 1/5988 | 9.652 |
| Ssp I | 1/8745 | 9.652 |
| StuI | 1/4844 | 9.652 |

The vectors of the present invention will be particularly useful in expression of genes in *Rhodococcus* sp and other like bacteria. Species of *Rhodococcus* particularly suited for use with these vectors include but are not limited to *Rhodococcus equi, Rhodococcus erythropolis, Rhodococcus opacus, Rhodococcus rhodochrous, Rhodococcus globerulus, Rhodococcus koreensis, Rhodococcus fascians*, and *Rhodococcus ruber*.

Methods for Gene Expression

Applicants' invention provides methods for gene expression in host cells, particularly in the cells of microbial hosts. Expression in recombinant microbial hosts may be useful for the expression of various pathway intermediates; for the modulation of pathways already existing in the host for the synthesis of new products heretofore not possible using the host. Additionally the gene products may be useful for conferring higher growth yields of the host or for enabling alternative growth mode to be utilized.

Once suitable plasmids are constructed they are used to transform appropriate host cells. Introduction of the plasmid into the host cell may be accomplished by known procedures such as by transformation, e.g., using calcium-permeabilized cells, electroporation, transduction, or by transfection using a recombinant phage virus. (Maniatis, supra)

In a preferred embodiment the present vectors may be co-transformed with additional vectors, also containing DNA heterologus to the host. It will be appreciated that both the present vector and the additional vector will have to reside in the same incompatibility group. The ability for two or plasmids to coexist in same host will depend on whether they belong to the same incompatibility group. Generally, plasmids that do not compete for the same metabolic elements will be compatible in the same host. For a compete review of the issues surrounding plasmid coexistence see Thomas et al., *Annu. Rev. Microbiol.* (1987), 41, 77–101. Vectors of the present invention comprise the rep protein coding sequence as set forth in SEQ ID NO:1 and the ORI sequence as set forth in SEQ ID NO:8. Any vector containing the instant rep coding sequence and the ORI will be expected to replicate in *Rhodococcus*. Any plasmid that has the ability to co-exist with the rep expressing plasmid of the present invention is in the different compatibility group as the instant plasmid and will be useful for the co-expression of heterologus genes in a specified host.

*Rhodococcus* Transformants as Microbial Production Platform

Once a suitable *Rhodococcus* host is successfully transformed with the appropriate vector of the present invention it may be cultured in a variety of ways to allow for the commercial production of the desired gene product. For example, large scale production of a specific gene product, overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of the instant proteins may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "µL" means microliter(s), "mL" means milliliter(s), "L" means liter(s), "µM" means micromolar, "mM" means millimolar, "µg" means microgram(s), "mg" means milligram(s), "psi" means pounds per square inch, "ppm" means parts per million, "A" means adenine or adenosine, "T" means thymine or thymidine, "G" means guanine or guanosine, "C" means cytidine or cytosine, "x g" means times gravity, "nt" means nucleotide(s), "aa" means amino acid(s), "bp" means base pair(s), and "kb" means kilobase(s).

Isolation of *Rhodococcus erthyopolis* AN12

The present *Rhodococcus erythropolis* AN12 strain was isolated from wastestream sludge as described below in Example 1.

Preparation of Genomic DNA for Sequencing and Sequence Generation

Genomic DNA was isolated from *Rhodococcus erythropolis* AN12 according to standard protocols.

Genomic DNA and library construction were prepared according to published protocols (Fraser et al The Minimal Gene Complement of Mycoplasma genitalium; *Science* 270, 1995). A cell pellet was resuspended in a solution containing 100 mM Na-EDTA pH 8.0, 10 mM Tris-HCl pH 8.0, 400 mM NaCl, and 50 mM MgCl2.

Genomic DNA Preparation

After resuspension, the cells were gently lysed in 10% SDS, and incubated for 30 minutes at 55° C. After incubation at room temperature, proteinase K (Boehringer Mannheim, Indianapolis, Ind.) was added to 100 µg/ml and incubated at 37° C. until the suspension was clear. DNA was extracted twice with Tris-equilibrated phenol and twice with chloroform. DNA was precipitated in 70% ethanol and resuspended in a solution containing 10 mM Tris-HCl and 1 mM Na-EDTA (TE buffer) pH 7.5. The DNA solution was treated with a mix of RNAases, then extracted twice with Tris-equilibrated phenol and twice with chloroform. This was followed by precipitation in ethanol and resuspension in TE.

Library Construction 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease (New England Biolabs, Beverly, Mass.). After size fractionation, a fraction (2.0 kb, or 5.0 kb) was excised, cleaned and a two-step ligation procedure was used to produce a high titer library with greater than 99% single inserts.

Sequencing

A shotgun sequencing strategy approach was adopted for the sequencing of the whole microbial genome (Fleischmann, Robert et al Whole-Genome Random sequencing and assembly of *Haemophilus influenzae* Rd *Science*, 269:1995).

Sequence was generated on an ABI Automatic sequencer using dye terminator technology (U.S. Pat. No. 5,366,860; EP 272007) using a combination of vector and insert-specific primers. Sequence editing was performed in either Sequencher (Gene Codes Corporation., Ann Arbor, Mich.) or the Wisconsin GCG program (Wisconsin Package Version 9.0, Genetics Computer Group (GCG), Madison, Wis.) and the CONSED package (version 7.0). All sequences represent coverage at least two times in both directions.

Identification and Characterization of repA Coding Regions

DNA encoding the repA protein was identified by conducting BLAST (Basic Local Alignment Search Tool; Altschul, S. F., et al., (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. All comparisons were done using either the BLASTNnr or BLASTXnr algorithm. The results of the BLAST comparison is given in Table 4 that summarizes the sequences to which they have the most similarity. Table 4 displays data based on the BLASTXnr algorithm with values reported in expect values. The Expect value estimates the statistical significance of the match, specifying the number of matches, with a given score, that are expected in a search of a database of this size absolutely by chance.

Example 1

Isolation and Characterization of Strain AN12

This Example describes the isolation of strain AN12 of *Rhodococcus erythropolis* on the basis of being able to grow on aniline as the sole source of carbon and energy. Analysis of a 16S rRNA gene sequence indicated that strain AN12 was related to high G+C Gram positive bacteria belonging to the genus *Rhodococcus*.

Bacteria that grow on aniline were isolated from an enrichment culture. The enrichment culture was established by inoculating 1 ml of activated sludge into 10 ml of S12 medium (10 mM ammonium sulfate, 50 mM potassium phosphate buffer (pH 7.0), 2 mM $MgCl_2$, 0.7 mM $CaCl_2$, 50 $\mu$M $MnCl_2$, 1 $\mu$M $FeCl_3$, 1 $\mu$M $ZnCl_3$, 1.72 $\mu$M $CuSO_4$, 2.53 $\mu$M $CoCl_2$, 2.42 $\mu$M $Na_2MoO_2$, and 0.0001% $FeSO_4$) in a 125 ml screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 ml of the culture with the same volume of S12 medium. Bacteria that utilize aniline as a sole source of carbon and energy were isolated by spreading samples of the enrichment culture onto S12 agar. Aniline was placed on the interior of each petri dish lid. The petri dishes were sealed with parafilm and incubated upside down at room temperature (25° C.). Representative bacterial colonies were then tested for the ability to use aniline as a sole source of carbon and energy. Colonies were transferred from the original S12 agar plates used for initial isolation to new S12 agar plates and supplied with aniline on the interior of each petri dish lid. The petri dishes were sealed with parafilm and incubated upside down at room temperature (25° C.).

The 16S rRNA genes of each isolate were amplified by PCR and analyzed as follows. Each isolate was grown on R2A agar (Difco Laboratories, Bedford, Mass.). Several colonies from a culture plate were suspended in 100 $\mu$l of water. The mixture was frozen and then thawed. The 16S rRNA gene sequences were amplified by PCR by using a commercial kit according to the manufacturer's instructions (Perkin Elmer) with primers HK12 (5'-GAGTTTGATCCTGGCTCAG-3') (SEQ ID NO:9) and HK13 (5'-TACCTTGTTACGACTT-3') (SEQ ID NO:10). PCR was performed in a Perkin Elmer GeneAmp 9600. The samples were incubated for 5 minutes at 94° C. and then cycled 35 times at 94° C. for 30 seconds, 55° C. for 1 minute, and 72° C. for 1 minute. The amplified 16S rRNA genes were purified using a commercial kit according to the manufacturer's instructions (QIAquick PCR Purification Kit) and sequenced on an automated ABI sequencer. The sequencing reactions were initiated with primers HK12, HK13, and HK14 (5'-GTGCCAGCAGYMGCGGT-3') (SEQ ID NO:11, where Y=C or T, M=A or C). The 16S rRNA gene sequence of each isolate was used as the query sequence for a BLAST search [Altschul, et al., *Nucleic Acids Res*. 25:3389–3402(1997)] of GenBank for similar sequences.

A 16S rRNA gene of strain AN12 was sequenced (SEQ ID NO:12) and compared to other 16S rRNA sequences in the GenBank sequence database. The 16S rRNA gene sequence from strain AN12 was at least 98% homologous to the 16S rRNA gene sequences of high G+C Gram positive bacteria belonging to the genus *Rhodococcus*.

Example 2

Isolation and Partial Sequencing of Plasmid DNA from Strain AN12

The presence of small plasmid DNA in the *Rhodococcus* AN12 strain isolated as described in Example 1 was suggested by Applicants' observation of a low molecular weight DNA contamination in a genomic DNA preparation from AN12. Plasmid DNA was subsequently isolated from AN12 strain using a modified Qiagen plasmid purification protocol outlined as follows. AN12 was grown in 25 ml of NBYE medium (0.8% Nutrient Broth, 0.5% Yeast Extract and 0.05% Tween80) at 30° C. for 24 hours. The cells were centrifuged at 3850×g for 30 min. The cell pellet was washed with 50 mM sodium acetate (pH 5) and 50 mM sodium bicarbonate and KCl (pH 10). The cell pellet was then resuspended in 5 ml Qiagen P1 solution with 100 $\mu$g/ml RNaseA and 2 mg/ml lysozyme and incubated at 37° C. for 30 min to ensure cell lysis. Five ml of Qiagen P2 and 7 ml of Qiagen N3 solutions were added to precipitate chromosomal DNA and proteins. Plasmid DNA was recovered by the addition of 12 ml of isopropanol. The DNA was washed and resuspended in 800 $\mu$l of water. This DNA was loaded onto a Qiagen miniprep spin column and washed twice with 500 $\mu$l PB buffer followed by one wash with 750 $\mu$l of PE buffer to further purify the DNA. The DNA was eluted with 100 $\mu$l of elution buffer. An aliquot of the DNA sample was examined on a 0.8% agarose gel and a small molecular weight DNA band was observed.

The DNA was then digested with a series of restriction enzymes and a restriction map of pAN12 is presented in FIG. 1. While HindIII cleaves pAN12 at three sites (see Table 1), only the two larger bands were recovered for further analysis. These two HindIII generated bands, one of 1.7 kb and one of 4.4 kb, were excised from the agarose gel and cloned into the HindIII site of pUC19 vector. The ends of both inserts were sequenced from the pUC constructs using the M13 universal primer (−20; GTAAAACGACGGCCAGT) (SEQ ID NO:13) and the M13 reverse primer (−48; AGCGGATAACAATTTCACACAGGA) (SEQ ID NO:14). Consensus sequences were obtained from the sequencing of two clones of each insert and comprise the nucleotide sequences as set forth in SEQ ID NOs:15–17. Sequence obtained from one end of the 4.4 kb insert was poor and is not shown. The HindIII recognition site is highlighted in bold and underlined in SEQ ID NOs:15–17.

Example 3

Complete Sequencing and Confirmation of a Cryptic Plasmid in Strain AN12

The sequences generated from the two HindIII fragments of the plasmid DNA were used to search the DuPont internal AN12 genome database. All three sequences had 100% match with regions of contig 2197 from assembly 4 of AN12 genomic sequences. Contig 2197 was 6334 bp in length. There were randomly sequenced clones in the database spanning both ends of contig 2197, indicating that this is a circular piece of DNA. Applicants have designated the 6334 bp circular plasmid from strain AN12 as pAN12. The complete nucleotide sequence of pAN12 designating the unique SspI site as the position 1 and is set forth in SEQ ID NO:5. One end of the 1.7 kb HindIII insert (SEQ ID NO:15) matched with the 6313–5592 bp region of the complement strand of pAN12 sequence (SEQ ID NO:5). Another end of the 1.7 kb HindIII insert (SEQ ID NO:16) matched with the 4611–5133 bp region of pAN12 sequence (SEQ ID NO:5). One end of the 4.4 kb HindIII insert (SEQ ID NO:17) matched with the 4616–4011 bp region of the complement strand of pAN12 sequence (SEQ ID NO:5). Three HindIII restriction sites were predicted to be on the pAN12 plasmid based on the complete sequence. Three restriction fragments generated from HindIII digest should be in sizes as 4550 bp, 1687 bp and 87 bp. The 4.4 kb and 1.7 kb bands Applicants observed on the gel matched well with the predicated 4550 bp and 1687 bp fragments. The 87 bp fragment would not be easily detected on a 0.8% agarose gel. The copy number of the pAN12 plasmid was estimated to be around 10 copies per cell, based on the statistics that contig 2197 was sequenced at 80× coverage comparing to average about 8× coverage of other contigs representing chromosomal sequences.

BLASTX analysis showed that two open reading frames (ORFs) encoded on pAN12 shared some homology with proteins in the "nr" database (comprising all non-redundant GenBank CDS translations, sequences derived from the 3-dimensional structure Brookhaven Protein Data Bank, SWISS-PROT protein sequence database, EMBL, and DDBJ databases). One ORF (designated rep) at the complement strand of nucleotides 3052–1912 of SEQ ID NO:5 showed the greatest homology to replication protein of plasmid pAP1 from *Arcanobacterium pyogenes* (Billington, S. J. et al, *J. Bacteriol.* 180, 3233–3236, 1998). The second ORF (designated div) at the complement strand of nucleotides 5179–4288 of SEQ ID NO:5 showed the greatest homology to a putative cell division protein from *Haemophilus influenzae* identified by genomic sequencing (Fleischmann et al., *Science* 269 (5223), 496–512 (1995). The rep nucleic acid (SEQ ID NO:1) on pAN12 is predicted to encode a Rep protein of 379 amino acids in length (SEQ ID NO:2). It shares a 51% identity and a 35% similarity to the 459 amino acid Rep protein from *Arcanobacterium* (see Table 4). The div nucleic acid (SEQ ID NO:3) on pAN12 is predicted to encode a Div protein of 296 amino acids in length (SEQ ID NO:4). It shares only a 24% identity and a 40% similarity to the internal portion of the 529 amino acid putative cell division protein from *Haemophilus* (see Table 4).

TABLE 4

BLASTX analysis of the two pAN12 open reading frames (ORFs)

| ORF | Similarity Identified | % Identity[a] | % Similarity[b] | E-value[c] | Citation |
|---|---|---|---|---|---|
| rep | Gb\|AAC46399.1\| (U83788) Replication protein [*Arcanobacterium pyogeness*] | 35 | 51 | e-59 | Billington et al J. Bacteriol. 180 (12), 3233–3236 (1998) |
| div | sp\|P45264\| (U32833) Cell division protein ftsK homolog [*Haemophilus influenzae*] | 24 | 40 | 2e-4 | Fleischmann et al Science 269 (5223), 496–512 (1995) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Example 4

Construction of an *Escherichia Coli-Rhodococcus* Shuttle Vector with the Cryptic Pan12 Plasmid An *E. coli-Rhodococcus* shuttle vector requires a set of replication function and antibiotic resistance markers that functions both in *E. coli* and in *Rhodococcus*. Applicants have identified a cryptic pAN12 plasmid which encodes the replication function for *Rhodococcus*. To identify an antibiotic resistance marker for *Rhodococcus*. The on *E. coli* plasmid pBR328 (ATCC 37517) was tested to see whether it would function in *Rhodococcus*. Plasmid pBR328 carries ampicillin, chloramphenicol and tetracycline resistance markers that function in *E. coli*. pBR328 was linearized with PvuII which disrupted the chloramphenicol resistance gene and ligated with pAN12 digested with SspI. The resulting clone was designated pRhBR17 (SEQ ID NO:6).

pRhBR17 was confirmed to be ampicillin resistant, chloramphenicol sensitive and tetracycline resistant in *E. coli*. DNA of pRhBR17 was prepared from *E. coli* DH10B (GIBCO, Rockville, Md.) and electroporated into *Rhodococcus erythropolis* (ATCC 47072) which does not contain the pAN12 plasmid. The electrocompetent cells of ATCC 47072 were prepared as follows:

ATCC 47072 was grown in NBYE (0.8% nutrient broth and 0.5% yeast extract)+Tween 80 (0.05%) medium at 30° C. with aeration to an OD600 of about 1.0. Cells were cooled at 4° C. for more than 30 minutes before they were pelleted by centrifugation. Pellets were washed with ice cold sterile water three times and ice cold sterile 10% glycerol twice and resuspended in 10% glycerol as aliquots for quick freeze. Electroporation was performed with 50 µl of competent cells mixed with 0.2–2 µg of plasmid DNA. The electroporation setting used was similar to *E. coli* electroporation: 200 ohms, 25 µF and 2.5 kV for 0.2 cm gap cuvette. After an electroporation pulse, 0.5–1 mL of NBYE medium was immediately added and cells were recovered on ice for at least 5 minutes. The transformed cells were incubated at 30° C. for 4 hours to express the antibiotic resistance marker and plated on NBYE plates with 5 µg/ml of tetracycline. Tetracycline resistance transformants were obtained when ATCC 47072 was transformed with pRhBR17. No tetracycline resistant colony was obtained for mock transformation of ATCC 47072 with sterile water. The results suggested that the tetracycline resistance marker on pBR328 functioned in *Rhodococcus* and the plasmid pRhBR17 was able to shuttle between *E. coli* and *Rhodococcus*. The transformation frequency was about $10^6$ colony forming units (cfu)/µg of DNA for ATCC 47072. The shuttle plasmids were also able to transform the AN12 strain containing the indigenous pAN12 cryptic plasmid at about 10-fold lower frequency.

Example 5 pAN12 Replicon is Compatible with Nocardiophage Q4 Replicon of pDA71

Figure 4:
FIG. 4A is an alignment of amino acid sequences of various replication proteins of pIJ101/pJV1 family of rolling circle replication plasmids.
FIG. 4B is an alignment of nucleotide sequences for various origins of replication of the rolling circle replication plasmids.

The replicon is a genetic element that behaves as an autonomous unit during replication. To identify and confirm the essential elements such as the replication protein and origin of replication that define the function of the pAN12 replicon, the pAN12 sequence was further examined by multiple sequence alignment with other plasmids. Although Rep of pAN12 had only 35% overall amino acid identity to Rep of *Arcanobacterium* plasmid pAP1, five motifs were identified in pAN12 Rep that are conserved in the pIJ101/pJV1 family of rolling circle replication plasmids including pAP1 (Ilyina, T. V. et al *Nucleic Acids Research*, 20:3279–3285; Billington, S. J. et al, *J. Bacteriol.* 180, 3233–3236, 1998) through ClustalW multiple sequence alignment (FIG. 4A). Some of the other members in this family of plasmids include pIJ101 from *Streptomyces lividans* (Kendall, K. J. et al, *J. Bacteriol.* 170:4634–4651, 1988), pJV1 from *Streptomyces phaeochromogenes* (Servin-Gonzalez, L. *Plasmid.* 30:131–140, 1993; Servin-Gonzalez, L. *Microbiology.* 141:2499–2510,1995) and pSN22 from *Streptomyces nigrifaciens* (Kataoka, M. et al. *Plasmid.* 32:55–69, 1994). The numbers in FIG. 4A indicate the starting amino acid for each motif within the Rep. Also identified were the putative origin of replication (Khan, S. A. *Microbiol. and Mol. Biology Reviews.* 61:442–455,1997) in pAN12 through multiple sequence alignment (FIG. 4B). The numbers in FIG. 4B indicate the positions of the first nucleotide on the plasmid for the origins of replication. The origins of replication in pIJ101, pJV1 and pSN22 have been previously confirmed experimentally (Servin-Gonzalez, L. Plasmid. 30:131–140, 1993; Suzuki, I. et al., *FEMS Microbiol. Lett.* 150:283–288, 1997). The GG dinucleotides at the position of the nick site where the replication initiates are also conserved in pAN12.

The pAN12 replicon was found to be compatible with at least one other *Rhodococcus* replicon Q4 derived from nocardiophage (Dabbs, 1990, *Plasmid* 23:242–247). pDA71 is a *E. coli-Rhodococcus* shuttle plasmid constructed based on the nocardiophage Q4 replicon and carries a chloramphenicol resistance marker that expresses in *Rhodococcus* (ATCC 77474, Dabbs, 1993, *Plasmid* 29;74–79). Transformation of pDA71 into *Rhodococcus erythropolis* strain AN12 and subsequent plasmid DNA isolation from the transformants indicated that the chloramphenicol resistant pDA71 plasmid (~9 kb) coexisted with the 6.3 kb indigenous pAN12 plasmid in AN12 strain. Additionally the order of the plasmid introduction into the host was reversed. The chloramphenicol resistant pDA71 was first introduced into the plasmid free *Rhodococcus erythropolis* strain ATCC 47072. Competent cells were prepared from a chloramphenicol resistant transformant of ATCC 47072(pDA71) and then transformed with the tetracycline resistant pRhBR17 shuttle plasmid constructed based on the pAN12 replicon (Example 4). Transformants of both chloramphenicol and tetracycline resistance were isolated, suggesting both pDA71 and pRhBR17 were maintained in the ATCC 47072 host. The compatibility of pAN12 replicon with the nocardiophage Q4 replicon could be exploited for co-expression of different genes in a single *Rhodococcus* host using shuttle plasmids derived from pAN12 replicon such as pRhBR17 and shuttle plasmids derived from the nocardiophage Q4 replicon such as pDA71.

Example 6

Rep on pAN12 is Essential for Shuttle Vector Function

The previous examples demonstrated that pAN12 provides the replication function in *Rhodococcus* for the constructed shuttle plasmid. To characterize the essential region of pAN12 for shuttle plasmid function, Applicants performed in vitro transposon mutagenesis of the shuttle plasmids, pRhBR17, using the GPS-1 genome priming system from New England Biolabs (Beverly, Mass.). The in vitro transposition reaction was performed following manufacturer's instructions. The resulting transposon insertions of pRhBR17 were transformed into *E. coli* DH10B (GIBCO, Rockville, Md.) and kanamycin resistant colonies were selected by plating on LB agar plates comprising 25 µg/ml of kanamycin. Transposon insertions in the ampicillin resistance and tetracycline resistance genes were screened out by sensitivity to ampicillin and tetracycline, respectively. Plasmid DNA from 34 of the ampicillin resistant, tetracycline resistant and kanamycin resistant colonies were purified and the insertion sites were mapped by sequencing using the Primer N (ACTTTATTGTCATAGTTTAGATCTATTTTG; SEQ ID NO:18) complementary to the right end of the transposon. Applicants also tested the ability of the shuttle plasmids comprising the transposon insertions to transform *Rhodococcus* ATCC 47072. Table 5 summarizes the data of insertion mapping and transformation ability. The insertion site on Table 5 refers to the base pair (bp) numbering on the shuttle plasmid pRhBR17 (SEQ ID NO:6), which uses the position 1 of pBR328 as the position 1 of the shuttle plasmid. High quality junction sequence was obtained for most of the insertions so that the exact location of the transposon insertions could be identified on the plasmids. In clones 17, 33 and 37, the sequence of the transposon ends could not be identified to map the exact insertion sites.

TABLE 5

Transposon insertion mapping of pRhBR17 and the effects on transformation of *Rhodococcus* ATCC 47072

| Clone number | Site inserted | Strand inserted | Gene inserted | Transformation ability |
|---|---|---|---|---|
| pRhBR17 | No insertion | N/A | N/A | +++ |
| 30, 31 | 2092 bp | Forward | pBR328 | +++ |
| 26, 27 | 3120 bp | Reverse | pBR328 | ND |
| 29 | 3468 bp | Reverse | pBR328 | ND |
| 24 | 3625 bp | Reverse | pAN12 | +++ |
| 2 | 4030 bp | Reverse | pAN12 | +++ |
| 38, 39 | 4114 bp | Forward | pAN12 | +++ |
| 20 | 4442 bp | Reverse | pAN12 | +++ |
| 1 | 4545 bp | Reverse | pAN12 | +++ |
| 35 | 4568 bp | Forward | pAN12 | +++ |
| 13 | 4586 bp | Forward | pAN12 | + |
| 17, 33 | <4920 bp | Forward | pAN12 | + |
| 7 | 5546 bp | Forward | pAN12 rep | + |
| 11 | 5739 bp | Reverse | pAN12 rep | − |
| 12 | 5773 bp | Forward | pAN12 rep | − |
| 16 | 5831 bp | Forward | pAN12 rep | − |
| 5 | 5883 bp | Reverse | pAN12 rep | − |
| 9 | 6050 bp | Reverse | pAN12 rep | − |
| 28 | 6283 bp | Forward | pAN12 rep | − |
| 6 | 6743 bp | Reverse | pAN12 | − |
| 37 | <6935 bp | Forward | pAN12 | +++ |
| 32 | 6965 bp | Forward | pAN12 | +++ |
| 15 | 6979 bp | Forward | pAN12 | + |
| 3 | 7285 bp | Reverse | pAN12 | +++ |
| 4 | 7811 bp | Reverse | pAN12 | +++ |
| 22, 23 | 8274 bp | Forward | pAN12 div | +++ |
| 21 | 8355 bp | Forward | pAN12 div | +++ |
| 18 | 8619 bp | Reverse | pAN12 div | +++ |
| 10 | 10322 bp | Reverse | pBR328 | +++ |
| 36 | 11030 bp | Forward | pBR328 | ND |

+++ the transformation frequency was comparable to that of the wild type plasmid.
+ the transformation frequency decreased about 100 fold.
− the transformation frequency was zero.
ND the transformation frequency was not determined.

Transposon insertions at most sites of the shuttle plasmid did not abolish the ability of the plasmids to transform *Rhodococcus* ATCC 47072. The insertions that abolished the shuttle plasmid function were clustered at the rep region. Clones 5, 9, 11, 12, 16, and 28 all contained transposon insertions that mapped within the rep gene of pAN12. These mutant plasmids were no longer able to transform *Rhodococcus* ATCC 47072. Clone 6 contained an insertion at 6743 bp, which is 100 bp upstream of the start codon (6642 bp) of the Rep region. This insertion also disrupted the shuttle plasmid function since it most likely interrupted the transcription of the rep promoter. Clone 7 contained an insertion at 5546 bp, which is very close to the C terminal end (5502 bp) of the Rep region. The transformation frequency of this plasmid was decreased by at least 100 fold. This is likely due to the residual activity of the truncated Rep which was missing 14 amino acids at the C terminal end because of the transposon insertion. In summary, the data indicated that the Rep region at the complement strand of nucleotides 3052–1912 of pAN12 (SEQ ID NO:5) was essential for shuttle plasmid function in *Rhodococcus*.

Example 7

Div on pAN12 is Involved in Maintaining Plasmid Stability

The transposon insertions within the div gene of pAN12 did not affect the ability of the shuttle plasmid to transform *Rhodococcus*. To determine if the putative cell division protein encoded by div played a role in cell division particularly plasmid partition, plasmid stability of *Rhodococcus* strain AN12 or ATCC 47072 comprising a pRhBR17 plasmid with different insertions was examined. After propagating the cells in NBYE+Tween80 medium with and without antibiotic selection (tetracycline at 10 µg/ml) for about 30 generations, dilutions ($10^{-4}$, $10^{-5}$ and $10^{-6}$) of cells were plated out on LB plates. Colonies grown on the nonselective LB plates were subsequently patched onto a set of LB and LB+tetracycline plates. Two hundred colonies of each were scored for tetracycline sensitivity. Representatives of the tetracycline sensitive cells were also examined to confirm the loss of the plasmid by PCR and plasmid isolation. The primers for PCR were designed based on the rep gene sequence of pAN12. A 1.1 kb PCR fragment could be obtained with Rep1 primer: 5'-ACTTGCGAACCGATATTATC-3' (SEQ ID NO:19) and Rep2 primer: 5'-TTATGACCAGCGTAAGTGCT-3' (SEQ ID NO:20) if the pAN12-based shuttle plasmid was present in the cell to serve as the template. The percentage of the plasmid maintained after 30 generations is summarized in Table 6. The wild type pRhBR17 plasmid was very stable in AN12 and slightly less stable in ATCC 47072. Clone #15 contained an insertion at the upstream region of the rep on pRhBR17 (Table 5) and showed slightly decreased stability in both AN12 and ATCC 47072 comparable to that of the wild type plasmid. Both the wild type pRhBR17 plasmid and the plasmid with insertion #15 were maintained 100% in the presence of the tetracycline selection in both *Rhodococcus* strains. In contrast, clone #23 contained an insertion that disrupted the putative cell division protein div and showed decreased plasmid stability. Loss of plasmid was observed even in the presence of the tetracycline selection. The stability was affected more in ATCC 47072 than in AN12. These results suggest that the putative cell division protein on pAN12 regulates plasmid partitioning during cell division and is important for maintaining plasmid stability.

TABLE 6

Plasmid stability in *Rhodococcus* strains after 30 generations

| | AN12 without selection | AN12 with selection | ATCC 47072 without selection | ATCC 47042 with selection |
|---|---|---|---|---|
| WT pRhBR17 | 100% | 100% | 96.5% | 100% |
| Insertion #15 | 93% | 100% | 93% | 100% |
| Insertion #23 | 74% | 97% | 8.5% | 77.5% |

Example 8

Construction of pRHBR171 Shuttle Vector of Smaller Size

Transposon mutagenesis of the shuttle plasmid pRhBR17 suggested that certain regions of the shuttle plasmid may not be essential for the plasmid function (TABLE 5). One of the regions was at the junction of pBR328 and pAN12. It was decided to examine whether this region of the plasmid was dispensable and if the size of the shuttle plasmid could be trimmed. Shuttle plasmid pRhBR17 was digested with Pst I (2 sites/2520, 3700 bp) and mlu I (1 site/4105 bp), yielding three fragments of the following sizes: 9656, 1180 and 405 bp. The digested DNA fragments were blunted with mung bean nuclease (New England Biolabs, Beverly, Mass.) following manufacturer's instruction. The largest 9.7 kb fragment was separated by size on an agarose gel, and purified using QIAEX II Gel Extraction Kit (Qiagen Inc., Valencia, Calif.). This 9.7 kb DNA fragment with deletion of region 2520–4105 bp of pRhBR17 was self-ligated to form a circular plasmid designated pRhBR171 (FIG. 3). Plasmid isolation from the E. coli DH10B transformants and restriction enzyme characterization showed the correct size and digest pattern of pRhBR171. E. coli cells harboring the pRhBR171 plasmid lost the ability to grow in the presence of ampicillin (100 µg/ml), since the Pst I and Mlu I digest removed part of the coding region for the ampicillin resistant gene on the parental plasmid. The tetracycline resistance gene on pRhBR171 served as the selection marker for both E. coli and Rhodococcus. Transformation of pRhBR171 to Rhodococcus was tested. It transformed competent Rhodococcus erythropolis ATCC 47072 and AN12 cells with similar frequency by electroporation as compared with its parent plasmid pRhBR17. These results demonstrate that this region (2520–4105 bp) of pRhBR17 was not essential as suggested by transposon mutagenesis. It also provided a smaller shuttle vector that is more convenient for cloning.

Example 9

Increased Carotenoid Production with Multicopy Expression of Dxs on pRhBR171

The dxs gene encodes 1-deoxyxylulose-5-phosphate synthase that catalyzes the first step of the synthesis of 1-deoxyxylulose-5-phosphate from glyceraldehyde-3-phosphate and pyruvate precursors in the isoprenoid pathway for carotenoid synthesis. The putative dxs gene from AN12 was expressed on the multicopy shuttle vector pRhBR171 and the effect of dxs expression on carotenoid expression was evaluated.

The dxs gene with its native promoter was amplified from the Rhodococcus AN12 strain by PCR. Two upstream primers, New dxs 5' primer: 5'-ATT TCG TTG AAC GGC TCG CC-3' (SEQ ID NO:28) and New2 dxs 5' primer: 5'-CGG CAA TCC GAC CTC TAC CA-3' (SEQ ID NO:29), were designed to include the native promoter region of dxs with different lengths. The downstream primer, New dxs 3' primer: 5'-TGA GAC GAG CCG TCA GCC TT-3 (SEQ ID NO:30)' included the underlined stop codon of the dxs gene.

PCR amplification of AN12 total DNA using New dxs 5'+New dxs 3' yielded one product of 2519 bp in size, which included the full length AN12 dxs coding region and about 500 bp of immediate upstream region (nt. #500–#3019). When using New2 dxs 5'+New dxs 3' primer pair, the PCR product is 2985 bp in size, including the complete AN12 dxs gene and about 1 kb upstream region (nt. #34–#3019). Both PCR products were cloned in the pCR2.1-TOPO cloning vector according to manufacturer's instruction (Invitrogen, Carlsbad, Calif.). Resulting clones were screened and sequenced. The confirmed plasmids were digested with EcoRI and the 2.5 kb and 3.0 kb fragments containing the dxs gene and the upstream region from each plasmid were treated with the Klenow enzyme and cloned into the unique Ssp I site of the E. coli-Rhodococcus shuttle plasmid pRhBR171. The resulting constructs pDCQ22 (clones #4 and #7) and pDCQ23 (clones #10 and #11) were electroporated into Rhodococcus erythropolis ATCC 47072 with tetracycline 10 µg/ml selection.

The pigment of the Rhodococcus transformants of pDCQ22 and pDCQ23 appeared darker as compared with those transformed with the vector control. To quantify the carotenoid production of each Rhodococcus strain, 1 ml of fresh cultured cells were added to 200 ml fresh LB medium with 0.05% Tween-80 and 10 µg/ml tetracycline, and grown at 30° C. for 3 days to stationary phase. Cells were pelleted by centrifugation at 4000 g for 15 min and the wet weight was measured for each cell pellet. Carotenoids were extracted from the cell pellet into 10 ml acetone overnight with shaking and quantitated at the absorbance maximum (465 nm). 465 nm is the diagnostic absorbance peak for the carotenoid isloated from Rhodococcus sp. ATCC 47072. The absorption data was used to calculate the amount of carotenoid produced, calculated and normalized in each strain based either on the cell paste weight or the cell density (OD600). Carotenoid production calculated by either method showed about 1.6-fold increase in ATCC47072 with pDCQ22, which contained the dxs gene with the shorter promoter region.

Carotenoid production increased even more (2.2-fold) when the dxs gene was expressed with the longer promoter region. It is likely that the 1 kb upstream DNA contains the promoter and some elements for enhancement of the expression. HPLC analysis also verified that the same carotenoids were produced in the dxs expression strain as those of the wild type strain.

TABLE 2

Carotenoids production by Rhodococcus strains.

| Strain | OD600 | weight (g) | OD465 | %[a] | % (wt)[b] | % (OD600)[c] | % (avg)[d] |
|---|---|---|---|---|---|---|---|
| ATCC 47072 (pRhBR171) | 1.992 | 2.82 | 0.41 | 100 | 100 | 100 | 100 |
| ATCC (pDCQ22)#4 | 1.93 | 2.9 | 0.642 | 157 | 161 | 152 | 156 |
| ATCC (pDCQ22)#7 | 1.922 | 2.76 | 0.664 | 162 | 159 | 156 | 157 |
| ATCC (pDCQ23)#10 | 1.99 | 2.58 | 0.958 | 234 | 214 | 233 | 224 |
| ATCC (pDCQ23)#11 | 1.994 | 2.56 | 0.979 | 239 | 217 | 239 | 228 |

[a]% of carotenoid production based on OD465 nm.
[b]% of carotenoid production (OD465 nm) normalized with wet cell paste weight.
[c]% of carotenoid production (OD465 nm) normalized with cell density (OD600 nm).
[d]% of carotenoid production (OD465 nm) averaged from the normalizations with wet cell paste weight and cell density.

What is claimed is:

1. An isolated nucleic acid molecule comprising
   an isolated nucleic acid fragment encoding a plasmid replication protein having the amino acid sequence as set forth in SEQ ID NO:2.

2. The isolated nucleic acid of claim 1 as set forth in SEQ ID NO:1.

3. A plasmid comprising the nucleic acid of claim 1.

4. A plasmid according to claim 3 further comprising at least one nucleic acid encoding a selectable marker.

5. A plasmid according to claim 3 further comprising an origin of replication that is functional in a gram positive bacterium.

6. A plasmid according to claim 5 wherein the gram positive bacterium is a member of the Actinomycetales bacterial family.

7. A plasmid according to claim 6 wherein the gram positive bacterium is selected from the group consisting of, *Actinomyces, Actinoplanes, Arcanobacterium, Corynebacterium, Dietzia, Gordonia, Mycobacterium, Nocardia, Rhodococcus, Tsukamurella, Brevibacterium, Arthrobacter, Propionibacterium, Streptomyces Micrococcus*, and *Micromonospora*.

8. The plasmid according to claim 3 further comprising at least one promoter suitable for the expression of a gene in *Rhodococcus*.

9. A transformed bacteria comprising the plasmid of claim 3.

10. A transformed bacteria according to claim 9 wherein the bacteria is a member of the Actinomycetales bacterial family.

11. A transformed bacteria according to claim 10 wherein the bacteria is selected from the group consisting of, *Actinomyces, Actinoplanes, Arcanobacterium, Corynebacterium, Dietzia, Gordonia, Mycobacterium, Nocardia, Rhodococcus, Tsukamurella, Brevibacterium, Arthrobacter, Propionibacterium, Streptomyces, Micrococcus*, and *Micromonospora*.

12. A transformed bacteria, according to claim 11 selected from the group consisting of: *Rhodococcus equi, Rhodococcus erythropolis, Rhodococcus opacus, Rhodococcus rhodochrous, Rhodococcus globerulus, Rhodococcus koreensis, Rhodococcus fascians*, and *Rhodococcus ruber*.

13. A transformed bacteria of claim 9 comprising a second plasmid belonging to a different incompatibility group.

* * * * *

SEQUENCE LISTING

<160> NUMBER OF SEQ ID NOS: 30

<210> SEQ ID NO 1
<211> LENGTH: 1140
<212> TYPE: DNA
<213> ORGANISM: Rhodococcus AN12

<400> SEQUENCE: 1

| | | | | | |
|---|---|---|---|---|---|
| atgaccagcg | taagtgctga | acacctttcc | ggcaaagacc | ggcctcccgt | cctcgtgtcg | 60 |
| tccgataagc | gcggcatccg | gcacgaactg | cgacccaaac | ttcaacaaat | caccacgtca | 120 |
| gaaacattta | cgcctgtggt | ccggccgatt | tctggcgtga | acggtgtgac | cattgtcaac | 180 |
| ggtccgaaag | gttctggatt | cggaggcctt | cgttcctgcg | gaaagggctg | gatctgcccc | 240 |
| tgctgtgcgg | gaaaagtcgg | tgcacatcgt | gcagacgaaa | tttctcaagt | tgttgctcat | 300 |
| caactcggga | ctggatctgt | tgcgatggtg | acgatgacca | tgcgccatac | agctggtcag | 360 |
| cggctccacg | acctatggac | tggactttcg | gcagcctgga | aagctgcgac | caacggtcgt | 420 |
| cgttggcgta | cggaacgtga | aatgtacggc | tgcgacggat | acgtgcgcgc | tgttgaaatc | 480 |
| actcacggaa | aaaacggctg | gcacgtccac | gttcacgcgc | tactcatgtt | cagtggtgac | 540 |
| gtgagtgaga | acatcctcga | atccttctcg | gatgcgatgt | tcgatcggtg | gacttccaaa | 600 |
| ctcgtatctc | tgggatttgc | tgcgccacta | cgtaattcgg | gtggtctcga | tgtacgaaag | 660 |
| atcggcggtg | aagctgatca | agttctcgct | gcgtatctga | cgaaaattgc | atctggcgtt | 720 |
| ggtatggagg | ttggtagtgg | cgacggaaaa | agtggtcgac | atggcaaccg | tgcaccctgg | 780 |
| gaaatcgctg | ttgatgcagt | gggcggggat | ccacaagcgt | tggaactgtg | gcgagaattt | 840 |
| gagtttggtt | cgatgggacg | tcgggcaatc | gcgtggtccc | gtggattgcg | tgcccgagct | 900 |
| ggtcttgggg | cagaactaac | agatgctcag | atcgttgagc | aggaagaatc | tgccccggtc | 960 |
| atggttgcga | tcattccggc | gcgatcgtgg | atgatgattc | ggacttgtgc | gccttacgtc | 1020 |
| ttcggcgaga | tcctcggact | cgtcgaagct | ggcgcgactt | gggaaaatct | tcgtgatcac | 1080 |
| ttgcattatc | gattgcccgc | agcggatgtg | cggcccccga | taatatcggt | tcgcaagtga | 1140 |

<210> SEQ ID NO 2
<211> LENGTH: 379
<212> TYPE: PRT
<213> ORGANISM: Rhodococcus AN12

<400> SEQUENCE: 2

Met Thr Ser Val Ser Ala Glu His Leu Ser Gly Lys Asp Arg Pro Pro
1               5                   10                  15

Val Leu Val Ser Ser Asp Lys Arg Gly Ile Arg His Glu Leu Arg Pro
                20                  25                  30

Lys Leu Gln Gln Ile Thr Thr Ser Glu Thr Phe Asn Ala Cys Gly Arg
            35                  40                  45

Pro Ile Ser Gly Val Asn Gly Val Thr Ile Val Asn Gly Pro Lys Gly
        50                  55                  60

Ser Gly Phe Gly Gly Leu Arg Ser Cys Gly Lys Gly Trp Ile Cys Pro
65                  70                  75                  80

Cys Cys Ala Gly Lys Val Gly Ala His Arg Ala Asp Glu Ile Ser Gln
                85                  90                  95

Val Val Ala His Gln Leu Gly Thr Gly Ser Val Ala Met Val Thr Met
            100                 105                 110

|     |     |     |     |     |     |     |     |     |     |     |     |     |
| --- | --- | --- | --- | --- | --- | --- | --- | --- | --- | --- | --- | --- |
| Thr | Met | Arg | His | Thr | Ala | Gly | Gln | Arg | Leu | His | Asp | Leu | Trp | Thr | Gly |
|     | 115 |     |     |     | 120 |     |     |     |     | 125 |     |     |

Thr Met Arg His Thr Ala Gly Gln Arg Leu His Asp Leu Trp Thr Gly
    115                 120                 125

Leu Ser Ala Ala Trp Lys Ala Ala Thr Asn Gly Arg Arg Trp Arg Thr
130             135                 140

Glu Arg Glu Met Tyr Gly Cys Asp Gly Tyr Val Arg Ala Val Glu Ile
145             150                 155                 160

Thr His Gly Lys Asn Gly Trp His Val His Val His Ala Leu Leu Met
                165                 170                 175

Phe Ser Gly Asp Val Ser Glu Asn Ile Leu Glu Ser Phe Ser Asp Ala
            180              185             190

Met Phe Asp Arg Trp Thr Ser Lys Leu Val Ser Leu Gly Phe Ala Ala
        195                 200             205

Pro Leu Arg Asn Ser Gly Leu Asp Val Arg Lys Ile Gly Gly Glu
    210                 215             220

Ala Asp Gln Val Leu Ala Ala Tyr Leu Thr Lys Ile Ala Ser Gly Val
225             230                 235                 240

Gly Met Glu Val Gly Ser Gly Asp Gly Lys Ser Gly Arg His Gly Asn
                245                 250                 255

Arg Ala Pro Trp Glu Ile Ala Val Asp Ala Val Gly Gly Asp Pro Gln
            260                 265             270

Ala Leu Glu Leu Trp Arg Glu Phe Glu Phe Gly Ser Met Gly Arg Arg
    275                 280             285

Ala Ile Ala Trp Ser Arg Gly Leu Arg Ala Arg Ala Gly Leu Gly Ala
    290                 295             300

Glu Leu Thr Asp Ala Gln Ile Val Glu Gln Glu Ser Ala Pro Val
305             310                 315             320

Met Val Ala Ile Ile Pro Ala Arg Ser Trp Met Met Ile Arg Thr Cys
                325                 330                 335

Ala Pro Tyr Val Phe Gly Glu Ile Leu Gly Leu Val Glu Ala Gly Ala
            340                 345             350

Thr Trp Glu Asn Leu Arg Asp His Leu His Tyr Arg Leu Pro Ala Ala
    355                 360             365

Asp Val Arg Pro Pro Ile Ile Ser Val Arg Lys
    370                 375

<210> SEQ ID NO 3
<211> LENGTH: 891
<212> TYPE: DNA
<213> ORGANISM: Rhodococcus AN12

<400> SEQUENCE: 3

```
atggatcaaa cagacacgat cccgattgcg attggatgga acgaactagc tcaacctgtc    60
atggtcgata tagccaaaga tgctgctcac tggctcattc aaggcaaaac ccgttccgga   120
aaatctcaat gcacctacaa cctgctcgca caggctggat cgaatcccgc tgtgcgtgtc   180
gtcggagtcg atcccacttc cgtcttacta gccccattcg tccaccgacg accggctgaa   240
ccgaacatcg agctcgggct gaacgatttt gacaaagtcc tccgagtgct ccagttcgtc   300
aaagcagaat ctgaccgacg aatcgagtgt ttctgggatc gacgcataga caaaatttcg   360
ttgttctcgc cagcactacc tctcatcctg ctcgtactgg aagaatttcc cggaatcatc   420
gagggcgcac aggatttcga tgcaaccaac ggtctgaaac cagcagacag atacgcaccc   480
cgcatcacat cgcttgttcg acagatcgct gctcagtctg ccaaagcagg catcagaatg   540
ttgctcttgg ctcaacgtgc ggaagcttcc atcgtgggtg aaacgcccg ctcgaacttc   600
```

```
gcggtgaaaa tgactctccg cgtagacgaa cctgaatctg tcaaaatgct gcacccaac    660 gcaacacctg aagagtgcgc actggtcgaa ggattcgtcc ctggtcaagg cttcttcgac    720
caacccggac tacggcgcca atgatccga acgttcgcg taggtgagta ctcgacctac     780
gcgagttacg tcgaaaacgc agacctcgcg tacgaagcca cactgaacat cgaccgagca    840
caacgaatga caatcgcctc ggaataccca catctcggcg acataggctg a             891
```

<210> SEQ ID NO 4
<211> LENGTH: 296
<212> TYPE: PRT
<213> ORGANISM: Rhodococcus AN12

<400> SEQUENCE: 4

```
Met Asp Gln Thr Asp Thr Ile Pro Ile Ala Ile Gly Trp Asn Glu Leu
 1               5                  10                  15

Ala Gln Pro Val Met Val Asp Ile Ala Lys Asp Ala Ala His Trp Leu
            20                  25                  30

Ile Gln Gly Lys Thr Arg Ser Gly Lys Ser Gln Cys Thr Tyr Asn Leu
        35                  40                  45

Leu Ala Gln Ala Gly Ser Asn Pro Ala Val Arg Val Gly Val Asp
    50                  55                  60

Pro Thr Ser Val Leu Leu Ala Pro Phe Val His Arg Arg Pro Ala Glu
 65                  70                  75                  80

Pro Asn Ile Glu Leu Gly Leu Asn Asp Phe Asp Lys Val Leu Arg Val
                85                  90                  95

Leu Gln Phe Val Lys Ala Glu Ser Asp Arg Arg Ile Glu Cys Phe Trp
            100                 105                 110

Asp Arg Arg Ile Asp Lys Ile Ser Leu Phe Ser Pro Ala Leu Pro Leu
        115                 120                 125

Ile Leu Leu Val Leu Glu Glu Phe Pro Gly Ile Ile Glu Gly Ala Gln
    130                 135                 140

Asp Phe Asp Ala Thr Asn Gly Leu Lys Pro Ala Asp Arg Tyr Ala Pro
145                 150                 155                 160

Arg Ile Thr Ser Leu Val Arg Gln Ile Ala Ala Gln Ser Ala Lys Ala
                165                 170                 175

Gly Ile Arg Met Leu Leu Leu Ala Gln Arg Ala Glu Ala Ser Ile Val
            180                 185                 190

Gly Gly Asn Ala Arg Ser Asn Phe Ala Val Lys Met Thr Leu Arg Val
        195                 200                 205

Asp Glu Pro Glu Ser Val Lys Met Leu His Pro Asn Ala Thr Pro Glu
    210                 215                 220

Glu Cys Ala Leu Val Glu Gly Phe Val Pro Gly Gln Gly Phe Phe Asp
225                 230                 235                 240

Gln Pro Gly Leu Arg Arg Gln Met Ile Arg Thr Val Arg Val Gly Glu
                245                 250                 255

Tyr Ser Thr Tyr Ala Ser Tyr Val Glu Asn Ala Asp Leu Ala Tyr Glu
            260                 265                 270

Ala Ala Leu Asn Ile Asp Arg Ala Gln Arg Met Thr Ile Ala Ser Glu
        275                 280                 285

Tyr Pro His Leu Gly Asp Ile Gly
    290                 295
```

<210> SEQ ID NO 5
<211> LENGTH: 6334
<212> TYPE: DNA

<213> ORGANISM: Rhodococcus AN12

<400> SEQUENCE: 5

```
attcagacca acaatcagtc caactagcaa ggcgacaacc ggtatcgcaa ttcgtgaaac      60
aagctttgtc atgcgtccgc gctcttacga gcaggtgcgg agacggccgc tgcaggcatt     120
ggaaccaaat tctccactgt gatggatagt gcgagacgat ccatgccagt catgtagggc     180
tgcacccaga caaggccttc tgctcggtag atcgtgccga agctgaacgg ctcgttcggc     240
gggttgatga cgtgcacgga tgctgtcttg tcagtcgcaa cagttccgtc cttgcgtgca     300
actcggagca atgcgccagt cgaatacttc acacggccgt cgggagtgag cttgtcctga     360
accggcttga tggggtcgtc cataccggct acgaacaccg ggaactgatc agcggtagtt     420
gcgacgggga gggacgttcc gagctgaaca ttcatgcgca ttcctttgat cgaggctggt     480
acagcttatg tctccggtgt ccatattcag cgacacgcgt tcatctacac tcaaaaccgt     540
acacatagtg tagccagctg tccagttttc gcacactacg ttagcaactg aacatatttt     600
gtggttgatc agtcaataag ctgtccatat ggacgagaaa gaggttcgcg cgatgattca     660
gcgcaaagaa accgaacgaa aaatgcaggt catcaagcag gcgtccgtgg atctgtcaca     720
ctcctggcag accattcaga acgcgcacga ctccacgact gtcgcaatgg agctacgaga     780
agccgggctt caacgcgaat tctggctaca agctctcgcg gacatcacat ctgttgtggg     840
aactgcctct gagctgcgca atctatttc ccgtttctc gttgacgagc ttgacgtcag     900
cagccgaacc gttgccaccg ttgcagatgt tcaccgtcg accatcagta cttggcgtgg     960
tgagcatgag tcatcgtaaa aacatcctct gacctgctat ggccccaatg atcacctatt    1020
accaaggcgg cggcttcgcc gccgctgcca gcaggctccc ccacctacgc gctccgcttc    1080
gctcgcgctt cggtgctccg cccgcaggcc caggagcgag tttgcgcctc gtttagtcca    1140
tctaaggggt tcctagctgg cttgaggtcg caacgcatcc tgaagtcgat cgaggagcag    1200
gaacgcatca tctcgatcca gcgtggtttc ttgaccataa atcgagaggt acacgcccat    1260
gacaacgcca tcgacgtcta ccgaagctgg attcgctgcg atgccaagag gacgttcgtt    1320
gatgctcatg tgatgggttt acctgcaaaa atagtcagca gccaaatcgg aggcggcggc    1380
ttcgccgccg ctgccagcag gctcccccac ctacgcgctc cgcttcgctc gcgcttcggt    1440
gctccgcccg caggcccagg agcgagtttg cgcctcgttt agtccatcta aggggttcct    1500
agctggcttg aggtcgcaac gcatcctgaa gtcgatcgag gagcaggaac gcatcatctc    1560
gatccagcgt ggtttcttga ccataaatcg agaggtacac gcccatgaca acgccatcga    1620
cgtctaccga agctggattc gctgcgatgc caagaggacg ttcgttgatg ctcatgtgat    1680
gggtttacct gcaaaaatag tcagcagcca atcggccgg cctttttcta tctgcccggt    1740
cagccccccg agaccaacca tgaaacaggc cgtctctctg tcaaggccaa gccgctacgc    1800
ggtgctatcg cagccctgac agagagacac ccagcttcag agcggcaagt atcgggggga    1860
tgccctcaag tgtggttcat gcgggtgaaa gttgttgctc agcaacgctt ttcacttgcg    1920
aaccgatatt atcgggggcc gcacatccgc tgcgggcaat cgataatgca agtgatcacg    1980
aagattttcc caagtcgcgc cagcttcgac gagtccgagg atctcgccga agacgtaagg    2040
cgcacaagtc cgaatcatca tccacgatcg cgccggaatg atcgcaacca tgaccggggc    2100
agattcttcc tgctcaacga tctgagcatc tgttagttct gccccaagac cagctcgggc    2160
acgcaatcca cggaccacg cgattgcccg acgtccatc gaaccaaact caaattctcg    2220
ccacagttcc aacgcttgtg gatccccgcc cactgcatca acagcgattt cccagggtgc    2280
```

-continued

```
acggttgcca tgtcgaccac tttttccgtc gccactacca acctccatac caacgccaga    2340
tgcaattttc gtcagatacg cagcgagaac ttgatcagct tcaccgccga tctttcgtac    2400
atcgagacca cccgaattac gtagtggcgc agcaaatccc agagatacga gtttggaagt    2460
ccaccgatcg aacatcgcat ccgagaagga ttcgaggatg ttctcactca cgtcaccact    2520
gaacatgagt agcgcgtgaa cgtggacgtg ccagccgttt tttccgtgag tgatttcaac    2580
agcgcgcacg tatccgtcgc agccgtacat ttcacgttcc gtacgccaac gacgaccgtt    2640
ggtcgcagct ttccaggctg ccgaaagtcc agtccatagg tcgtggagcc gctgaccagc    2700
tgtatggcgc atggtcatcg tcaccatcgc aacagatcca gtcccgagtt gatgagcaac    2760
aacttgagaa atttcgtctg cacgatgtgc accgactttt cccgcacagc aggggcagat    2820
ccagccettt ccgcaggaac gaaggcctcc gaatccagaa cctttcggac cgttgacaat    2880
ggtcacaccg ttcacgccag aaatcggccg gccacaggcg ttaaatgttt ctgacgtggt    2940
gatttgttga agtttgggtc gcagttcgtg ccggatgccg cgcttatcgg acgacacgag    3000
gacgggaggc cggtctttgc cggaaaggtg ttcagcactt acgctggtca taacgagcgg    3060
ggtcctagtc aagtaggagc ctcgaaggcg gcggcagggt ggtccaacac ccttcgtcgc    3120
cgctcgtatt ttcggagtaa atccagctag ttcagctcgg atactccact tcgaggttca    3180
tcgattattt ggttttatc cacttaacca gcagaaacag cgtttatcgc tgatctgctg    3240
gtcagtgcgg cgtgtcgggg gagtcgctag tccgcggcga gtccccatgc ttcgagaaca    3300
ccgaccttct cttctggggt tctgcttgtc ttcaccagtg catcgaacag acctcggtat    3360
tcacccaagt gttcaatatc gaatccggct tccctggcgt aatcagggt gtagtagcag    3420
cacatcgcag ccagaatctc ggacgattcg gcgcgttcac cagcatgaat ccaaccataa    3480
acgtcatgcc caccccatag atcaggccct cgatgatcgt aaatgccaac ggctagtcgg    3540
aggatgaata ccgtagcttc gtgcttcacg catcaaccct ctgatctgct gcactcagaa    3600
ttgcatgacc tcccgaatga ctgcataact cgtcgtagac ctgagcaacg aacgaaggcc    3660
gatcagcatt gtccatgaag agttggacga acttcggccg gacgaggcca atccacggcg    3720
cagtcaaagt ttcaaaatca tgtgcctcga ggtgctcatg cattgcaacc gcccatgcgg    3780
ccccctcgagc ggcgcaccag tctcgttcaa ctccctcgct gtccgaaatg tcgtatttaa    3840
ggcccagtga tcgtccaact tcggcagctg cgtcactggc acgtttccaa tcgtcaccgc    3900
gtaagtcgtt gagcttttcg agttcatcgc ctagaagcag ctcagacatt gcaaaaacgg    3960
tcatcgaact gacccatcgt ggaccgacta gtgcaccaag gtcgtcgtcg gtgatctgca    4020
tgccgcgaag ttcgtcgacg acagcttggc cttccaaacc tactctggcc ctgagtattt    4080
cagttattac gagatgatcg ttcggccagc ctgatttgat ccggagtgca gtcgttacga    4140
ctcgttccgt gggcaggttt cggcgtgagg cgagttttc tcctgcctca tgtgcaacct    4200
tctcaaattg ctgtcgaatg taggtgttta ccgggattgc gtctgtcggg tagccgatca    4260
aggtgtgtcc tcctgtgtgt tcggttgtca gcctatgtcg ccgagatgtg ggtattccga    4320
ggcgattgtc attcgttgtg ctcggtcgat gttcagtgcg gcttcgtacg cgaggtctgc    4380
gttttcgacg taactcgcgt aggtcgagta ctcacctacg cgaaccgttc ggatcatttg    4440
gcgccgtagt ccgggttggt cgaagaagcc ttgaccaggg acgaatcctt cgaccagtgc    4500
gcactcttca ggtgttgcgt tggggtgcag cattttgaca gattcaggtt cgtctacgcg    4560
gagagtcatt ttcaccgcga agttcgagcg ggcgtttcca cccacgatgg aagcttccgc    4620
```

```
acgttgagcc aagagcaaca ttctgatgcc tgctttggca gactgagcag cgatctgtcg    4680
aacaagcgat gtgatgcggg gtgcgtatct gtctgctggt ttcagaccgt tggttgcatc    4740
gaaatcctgt gcgccctcga tgattccggg aaattcttcc agtacgagca ggatgagagg    4800
tagtgctggc gagaacaacg aaattttgtc tatgcgtcga tcccagaaac actcgattcg    4860
tcggtcagat tctgctttga cgaactggag cactcggagg actttgtcaa aatcgttcag    4920
cccgagctcg atgttcggtt cagccggtcg tcggtgacga atggggcta gtaagacgga    4980 agtgggatcg actccgacga cacgcacagc gggattcgat ccagcctgtg cgagcaggtt    5040
gtaggtgcat tgagattttc cggaacgggt tttgccttga atgagccagt gagcagcatc    5100
tttggctata tcgaccatga caggttgagc tagttcgttc catccaatcg caatcgggat    5160
cgtgtctgtt tgatccatca ggcgtccgtg cttttgtcga acggaagatc cttttcttgc    5220
tcccaccagg gccgattgtc cccgagtatg ccgccggcct cttccttcaa tgtgccggcc    5280
gatgagtcct cgacgtcact gagccatgct gcatctcgtg cttgagaaat ggtgtctgca    5340
tcgatcagaa gtagctcgac ccgacgcggc tctactttgg tgaaactggc acgtagagca    5400
ccgaaagcat cggctatttt gaccgtcttc gatgtcatat cttcaccggt gatccctgtc    5460
ggaaggtcga aagcgactga tcgagtcaat ccgtcgtccg aaaatttgta gctacgaatg    5520
atgggaggct gccagagga gttgatcaga ccaagattgg ccgcagcacc tgcaacttcc    5580
ggggttcctc gccaccatcg agctgtacga cgtttgcgac gccgagcctt cgttgcctct    5640
ctcaggtaga ccattgccac aacgcacacc agcagcacac tgaccaaaag ccacatctga    5700
gcgtcgaaga tgtacagcag cagaagcaac agaaacgtag aggacagaat cgggtaatcg    5760 gcaattttg ccttgagttt tgctcgcaaa atttgccagg tggaacgtct tttaacctgg    5820
tcaccgcgtc gaacggcttc gtagttgctc atcggggcca ctccacaacg acattcggac    5880
tatctacttc gacttgctca tctacgttcc acaaccacga ttcgactgga acgagagcgc    5940
atcccgaggt tccattctga agattgcttt gcactcgatc actcatcaaa gtctctggaa    6000
ccgtctcagc ctctacgccc ttatgtaccg ggacaggggt attcacggtc aaatacactg    6060
cccgccagcc ctcaggcact ggcacgtcac cgcacgcgct ggtcttcgag tacggcgacg    6120
tgatgacctt tccatctggg ttagtccact ggatcccatc ggcgctcaat tccggattca    6180
ctcggatgta tccaggtatc tctctgcatg cactgacaga tggaacagaa cctgtcggaa    6240
gaggggatct gcaccaggtc accgttcgtt cagcccatga gtcccgacgc tcttgcattc    6300
cgctggaaag cttaatatct tgcgtgccaa caat                                6334
```

<210> SEQ ID NO 6
<211> LENGTH: 11241
<212> TYPE: DNA
<213> ORGANISM: Plasmid pRHBR17

<400> SEQUENCE: 6

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
ccgcccagtc ctgctcgctt cgctacttgg agccactatc gactacgcga tcatggcgac     360
cacacccgtc ctgtggatcc tctacgccgg acgcatcgtg gccggcatca ccggcgccac     420
```

-continued

```
aggtgcggtt gctggcgcct atatcgccga catcaccgat ggggaagatc gggctcgcca    480
cttcgggctc atgagcgctt gtttcggcgt gggtatggtg gcaggccccg tggccggggg    540
actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggcg gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg ccgcgttgct   1440
ggcgtttttc cataggctcc gcccccctga cgagcatcac aaaaatcgac gctcaagtca   1500
gaggtggcga aacccgacag gactataaag ataccaggcg tttccccctg gaagctccct   1560
cgtgcgctct cctgttccga ccctgccgct taccggatac ctgtccgcct ttctcccttc   1620
gggaagcgtg gcgctttctc atagctcacg ctgtaggtat ctcagttcgg tgtaggtcgt   1680
tcgctccaag ctgggctgtg tgcacgaacc ccccgttcag cccgaccgct gcgccttatc   1740
cggtaactat cgtcttgagt ccaacccggt aagacacgac ttatcgccac tggcagcagc   1800
cactggtaac aggattagca gagcgaggta tgtaggcggt gctacagagt tcttgaagtg   1860
gtggcctaac tacggctaca ctagaaggac agtatttggt atctgcgctc tgctgaagcc   1920
agttaccttc ggaaaaagag ttggtagctc ttgatccggc aaacaaacca ccgctggtag   1980
cggtggtttt tttgtttgca agcagcagat tacgcgcaga aaaaaggat ctcaagaaga    2040
tcctttgatc ttttctacgg ggtctgacgc tcagtggaac gaaaactcac gttaagggat   2100
tttggtcatg agattatcaa aaaggatctt cacctagatc cttttaaatt aaaaatgaag   2160
ttttaaatca atctaaagta tatatgagta aacttggtct gacagttacc aatgcttaat   2220
cagtgaggca cctatctcag cgatctgtct atttcgttca tccatagttg cctgactccc   2280
cgtcgtgtag ataactacga tacgggaggg cttaccatct ggccccagtg ctgcaatgat   2340
accgcgagac ccacgctcac cggctccaga tttatcagca ataaaccagc cagccggaag   2400
ggccgagcgc agaagtggtc ctgcaacttt atccgcctcc atccagtcta ttaattgttg   2460
ccgggaagct agagtaagta gttcgccagt taatagtttg cgcaacgttg ttgccattgc   2520
tgcaggcatc gtggtgtcac gctcgtcgtt tggtatggct tcattcagct ccggttccca   2580
acgatcaagg cgagttacat gatcccccat gttgtgcaaa aaagcggtta gctccttcgg   2640
tcctccgatc gttgtcagaa gtaagttggc cgcagtgtta tcactcatgg ttatggcagc   2700
actgcataat tctcttactg tcatgccatc cgtaagatgc ttttctgtga ctggtgagta   2760
```

```
ctcaaccaag tcattctgag aatagtgtat gcggcgaccg agttgctctt gcccggcgtc    2820
aacacgggat aataccgcgc cacatagcag aactttaaaa gtgctcatca ttggaaaacg    2880
ttcttcgggg cgaaaactct caaggatctt accgctgttg agatccagtt cgatgtaacc    2940
cactcgtgca cccaactgat cttcagcatc ttttactttc accagcgttt ctgggtgagc    3000
aaaaacagga aggcaaaatg ccgcaaaaaa gggaataagg gcgacacgga aatgttgaat    3060
actcatactc ttcctttttc aatattattg aagcatttat cagggttatt gtctcatgag    3120
cggatacata tttgaatgta tttagaaaaa taaacaaata ggggttccgc gcacatttcc    3180
ccgaaaagtg ccacctgacg tctaagaaac cattattatc atgacattaa cctataaaaa    3240
taggcgtatc acgaggccct ttcgtcttcg aataaatacc tgtgacggaa gatcacttcg    3300
cagaataaat aaatcctggt gtccctgttg ataccgggaa gccctgggcc aacttttggc    3360
gaaaatgaga cgttgatcgg cacgtaagag gttccaactt tcaccataat gaaataagat    3420
cactaccggg cgtattttt gagttatcga ttttcagg agctaaggaa gctaaaatgg    3480
agaaaaaaat cactggatat accaccgttg atatatccca atggcatcgt aaagaacatt    3540
ttgaggcatt tcagtcagtt gctcaatgta cctataacca gaccgttcag attcagacca    3600
acaatcagtc caactagcaa ggcgacaacc ggtatcgcaa ttcgtgaaac aagctttgtc    3660
atgcgtccgc gctcttacga gcaggtgcgg agacggccgc tgcaggcatt ggaaccaaat    3720
tctccactgt gatggatagt gcgagacgat ccatgccagt catgtagggc tgcacccaga    3780
caaggccttc tgctcggtag atcgtgccga agctgaacgg ctcgttcggc gggttgatga    3840
cgtgcacgga tgctgtcttg tcagtcgcaa cagttccgtc cttgcgtgca actcggagca    3900
atgcgccagt cgaatacttc acacggccgt cgggagtgag cttgtcctga accggcttga    3960
tggggtcgtc cataccggct acgaacaccg gaactgatc agcggtagtt gcgacgggga    4020
gggacgttcc gagctgaaca ttcatgcgag ttcctttgat cgaggctggt acagcttatg    4080
tctccggtgt ccatattcag cgacacgcgt tcatctacac tcaaaaccgt acacatagtg    4140
tagccagctg tccagttttc gcacactacg ttagcaactg aacatatttt gtggttgatc    4200
agtcaataag ctgtccatat ggacgagaaa gaggttcgcg cgatgattca gcgcaaagaa    4260
accgaacgaa aaatgcaggt catcaagcag gcgtccgtgg atctgtcaca ctcctggcag    4320
accattcaga acgcgcacga ctccacgact gtcgcaatgg agctacgaga agccgggctt    4380
caacgcgaat tctggctaca agctctcgcg gacatcacat ctgttgtggg aactgcctct    4440
gagctgcgca atctatttc ccgttttctc gttgacgagc ttgacgtcag cagccgaacc    4500
gttgccaccg ttgcagatgt ttcaccgtcg accatcagta cttggcgtgg tgagcatgag    4560
tcatcgtaaa aacatcctct gacctgctat ggccccaatg atcacctatt accaaggcgg    4620
cggcttcgcc gccgctgcca gcaggctccc ccacctacgc gctccgcttc gctcgcgctt    4680
cggtgctccg cccgcaggcc caggagcgag tttgcgcctc gtttagtcca tctaaggggt    4740
tcctagctgg cttgaggtcg caacgcatcc tgaagtcgat cgaggagcag gaacgcatca    4800
tctcgatcca gcgtggtttc ttgaccataa atcgagaggt acacgcccat gacaacgcca    4860
tcgacgtcta ccgaagctgg attcgctgcg atgccaagag gacgttcgtt gatgctcatg    4920
tgatgggttt acctgcaaaa atagtcagca gccaaatcgg aggcggcggc ttcgccgccg    4980
ctgccagcag gctcccccac ctacgcgctc cgcttcgctc gcgcttcggt gctccgcccg    5040
caggcccagg agcgagtttg cgcctcgttt agtccatcta aggggttcct agctggcttg    5100
aggtcgcaac gcatcctgaa gtcgatcgag gagcaggaac gcatcatctc gatccagcgt    5160
```

```
ggtttcttga ccataaatcg agaggtacac gcccatgaca acgccatcga cgtctaccga    5220
agctggattc gctgcgatgc aagaggacg ttcgttgatg ctcatgtgat gggtttacct    5280
gcaaaaatag tcagcagcca aatcggccgg cctttttcta tctgcccggt cagcccccg    5340 agaccaacca tgaaacaggc cgtctctctg tcaaggccaa gccgctacgc ggtgctatcg    5400
cagccctgac agagagacac ccagcttcag agcggcaagt atcgggggga tgccctcaag    5460
tgtggttcat gcgggtgaaa gttgttgctc agcaacgctt ttcacttgcg aaccgatatt    5520
atcgggggcc gcacatccgc tgcgggcaat cgataatgca agtgatcacg aagattttcc    5580
caagtcgcgc cagcttcgac gagtccgagg atctcgccga agacgtaagg cgcacaagtc    5640
cgaatcatca tccacgatcg cgccggaatg atcgcaacca tgaccggggc agattcttcc    5700
tgctcaacga tctgagcatc tgttagttct gccccaagac cagctcgggc acgcaatcca    5760
cgggaccacg cgattgcccg acgtcccatc gaaccaaact caaattctcg ccacagttcc    5820
aacgcttgtg gatccccgcc cactgcatca acagcgattt cccagggtgc acggttgcca    5880
tgtcgaccac ttttccgtc gccactacca acctccatac caacgccaga tgcaatttc    5940 gtcagatacg cagcgagaac ttgatcagct tcaccgccga tctttcgtac atcgagacca    6000
cccgaattac gtagtggcgc agcaaatccc agagatacga gtttggaagt ccaccgatcg    6060
aacatcgcat ccgagaagga ttcgaggatg ttctcactca cgtcaccact gaacatgagt    6120
agcgcgtgaa cgtggacgtg ccagccgttt ttccgtgag tgatttcaac agcgcgcacg    6180
tatccgtcgc agccgtacat ttcacgttcc gtacgccaac gacgaccgtt ggtcgcagct    6240
ttccaggctg ccgaaagtcc agtccatagg tcgtggagcc gctgaccagc tgtatggcgc    6300
atggtcatcg tcaccatcgc aacagatcca gtcccgagtt gatgagcaac aacttgagaa    6360
atttcgtctg cacgatgtgc accgacttt cccgcacagc aggggcagat ccagcccttt    6420
ccgcaggaac gaaggcctcc gaatccagaa cctttcggac cgttgacaat ggtcacaccg    6480
ttcacgccag aaatcggccg gccacaggcg ttaaatgttt ctgacgtggt gatttgttga    6540
agtttgggtc gcagttcgtg ccggatgccg cgcttatcgg acgacacgag gacgggaggc    6600
cggtctttgc cggaaaggtg ttcagcactt acgctggtca taacgagcgg ggtcctagtc    6660
aagtaggagc ctcgaaggcg gcgcagggt ggtccaacac ccttcgtcgc cgctcgtatt    6720
ttcggagtaa atccagctag ttcagctcgg atactccact tcgaggttca tcgattattt    6780 ggttttatc cacttaacca gcagaaacag cgtttatcgc tgatctgctg gtcagtgcgg    6840
cgtgtcgggg gagtcgctag tccgcggcga gtccccatgc ttcgagaaca ccgaccttct    6900
cttctggggt tctgcttgtc ttcaccagtg catcgaacag acctcggtat tcacccaagt    6960
gttcaatatc gaatccggct tccctggcgt aatcaggggt gtagtagcag cacatcgcag    7020
ccagaatctc ggacgattcg gcgcgttcac cagcatgaat ccaaccataa acgtcatgcc    7080 cacccccatag atcaggccct cgatgatcgt aaatgccaac ggctagtcgg aggatgaata    7140
ccgtagcttc gtgcttcacg catcaaccct ctgatctgct gcactcagaa ttgcatgacc    7200
tcccgaatga ctgcataact cgtcgtagac ctgagcaacg aacgaaggcc gatcagcatt    7260
gtccatgaag agttggacga acttcggccg gacgaggcca atccacgcg cagtcaaagt    7320 ttcaaaatca tgtgcctcga ggtgctcatg cattgcaacc gcccatgcgg cccctcgagc    7380
ggcgcaccag tctcgttcaa ctccctcgct gtccgaaatg tcgtatttaa ggcccagtga    7440
tcgtccaact tcggcagctg cgtcactggc acgtttccaa tcgtcaccgc gtaagtcgtt    7500
```

```
gagctttccg agttcatcgc ctagaagcag ctcagacatt gcaaaaacgg tcatcgaact   7560
gacccatcgt ggaccgacta gtgcaccaag gtcgtcgtcg gtgatctgca tgccgcgaag   7620
ttcgtcgacg acagcttggc cttccaaacc tactctggcc ctgagtattt cagttattac   7680
gagatgatcg ttcggccagc ctgatttgat ccggagtgca gtcgttacga ctcgttccgt   7740
gggcaggttt cggcgtgagg cgagtttttc tcctgcctca tgtgcaacct tctcaaattg   7800
ctgtcgaatg taggtgttta ccgggattgc gtctgtcggg tagccgatca aggtgtgtcc   7860
tcctgtgtgt tcggttgtca gcctatgtcg ccgagatgtg ggtattccga ggcgattgtc   7920
attcgttgtg ctcggtcgat gttcagtgcg gcttcgtacg cgaggtctgc gttttcgacg   7980
taactcgcgt aggtcgagta ctcacctacg cgaaccgttc ggatcatttg cgccgtagt    8040 ccgggttggt cgaagaagcc ttgaccaggg acgaatcctt cgaccagtgc gcactcttca   8100
ggtgttgcgt tggggtgcag cattttgaca gattcaggtt cgtctacgcg gagagtcatt   8160
ttcaccgcga agttcgagcg ggcgtttcca cccacgatgg aagcttccgc acgttgagcc   8220
aagagcaaca ttctgatgcc tgctttggca gactgagcag cgatctgtcg aacaagcgat   8280
gtgatgcggg gtgcgtatct gtctgctggt ttcagaccgt tggttgcatc gaaatcctgt   8340
gcgccctcga tgattccggg aaattcttcc agtacgagca ggatgagagg tagtgctggc   8400
gagaacaaca aaattttgtc tatgcgtcga tcccagaaac actcgattcg tcggtcagat   8460
tctgctttga cgaactggag cactcggagg actttgtcaa aatcgttcag cccgagctcg   8520
atgttcggtt cagccggtcg tcggtggacg aatggggcta gtaagacgga agtgggatcg   8580
actccgacga cacgcacagc gggattcgat ccagcctgtg cgagcaggtt gtaggtgcat   8640
tgagattttc cggaacgggt tttgccttga atgagccagt gagcagcatc tttggctata   8700
tcgaccatga caggttgagc tagttcgttc catccaatcg caatcgggat cgtgtctgtt   8760
tgatccatca ggcgtccgtg cttttgtcga acggaagatc ctttttcttgc tcccaccagg   8820 gccgattgtc cccgagtatg ccgccggcct cttccttcaa tgtgccggcc gatgagtcct   8880
cgacgtcact gagccatgct gcatctcgtg cttgagaaat ggtgtctgca tcgatcagaa   8940
gtagctcgac ccgacgcggc tctactttgg tgaaactggc acgtagagca ccgaaagcat   9000
cggctatttt gaccgtcttc gatgtcatat cttcaccggt gatccctgtc ggaaggtcga   9060
aagcgactga tcgagtcaat ccgtcgtccg aaaatttgta gctacgaatg atgggaggct   9120
gcccagagga gttgatcaga ccaagattgg ccgcagcacc tgcaacttcc ggggttcctc   9180
gccaccatcg agctgtacga cgtttgcgac gccgagcctt cgttgcctct ctcaggtaga   9240
ccattgccac aacgcacacc agcagcacac tgaccaaaag ccacatctga gcgtcgaaga   9300
tgtacagcag cagaagcaac agaaacgtag aggacagaat cgggtaatcg gcaattttg    9360 ccttgagttt tgctcgcaaa atttgccagg tggaacgtct tttaacctgg tcaccgcgtc   9420
gaacggcttc gtagttgctc atcggggcca ctccacaacg acattcggac tatctacttc   9480
gacttgctca tctacgttcc acaaccacga ttcgactgga acgagagcgc atcccgaggt   9540
tccattctga agattgcttt gcactcgatc actcatcaaa gtctctggaa ccgtctcagc   9600
ctctacgccc ttatgtaccg ggacaggggt attcacggtc aaatacactg cccgccagcc   9660
ctcaggcact ggcacgtcac cgcacgcgct ggtcttcgag tacggcgacg tgatgacctt   9720
tccatctggg ttagtccact ggatcccatc ggcgctcaat tccggattca ctcggatgta   9780
tccaggtatc tctctgcatg cactgacaga tggaacagaa cctgtcggaa gagggatct    9840 gcaccaggtc accgttcgtt cagcccatga gtcccgacgc tcttgcattc cgctggaaag   9900
```

-continued

```
cttaatatct tgcgtgccaa caatctggat attacggcct ttttaaagac cgtaaagaaa    9960
aataagcaca agttttatcc ggcctttatt cacattcttg cccgcctgat gaatgctcat   10020
ccggaattcc gtatggcaat gaaagacggt gagctggtga tatgggatag tgttcaccct   10080
tgttacaccg ttttccatga gcaaactgaa acgttttcat cgctctggag tgaataccac   10140
gacgatttcc ggcagtttct acacatatat tcgcaagatg tggcgtgtta cggtgaaaac   10200
ctggcctatt tccctaaagg gtttattgag aatatgtttt tcgtctcagc caatccctgg   10260
gtgagtttca ccagttttga tttaaacgtg gccaatatgg acaacttctt cgcccccgtt   10320
ttcaccatgg gcaaatatta tacgcaaggc gacaaggtgc tgatgccgct ggcgattcag   10380
gttcatcatg ccgtttgtga tggcttccat gtcggcagaa tgcttaatga attacaacag   10440
tactgcgatg agtggcaggg cggggcgtaa tttttttaag gcagttattg gtgcccttaa   10500
acgcctggtg ctacgcctga ataagtgata ataagcggat gaatggcaga aattcgaaag   10560
caaattcgac ccggtcgtcg gttcagggca gggtcgttaa atagccgctt atgtctattg   10620
ctggtttacc ggtttattga ctaccggaag cagtgtgacc gtgtgcttct caaatgcctg   10680
aggccagttt gctcaggctc tccccgtgga ggtaataatt gacgatatga tcatttattc   10740
tgcctcccag agcctgataa aaacggtgaa tccgttagcg aggtgccgcc ggcttccatt   10800
caggtcgagg tgcccggct ccatgcaccg cgacgcaacg cggggaggca gacaaggtat   10860
agggcggcgc ctacaatcca tgccaacccg ttccatgtgc tcgccgaggc ggcataaatc   10920
gccgtgacga tcagcggtcc agtgatcgaa gttaggctgg taagagccgc gagcgatcct   10980
tgaagctgtc cctgatggtc gtcatctacc tgcctggaca gcatggcctg caacgcgggc   11040
atcccgatgc cgccggaagc gagaagaatc ataatgggga aggccatcca gcctcgcgtc   11100
gcgaacgcca gcaagacgta gcccagcgcg tcggccgcca tgccggcgat aatggcctgc   11160
ttctcgccga aacgtttggt ggcgggacca gtgacgaagg cttgagcgag ggcgtgcaag   11220
attccgaata ccgcaagcga c                                             11241
```

<210> SEQ ID NO 7
<211> LENGTH: 9652
<212> TYPE: DNA
<213> ORGANISM: Plasmid pRHBR17

<400> SEQUENCE: 7

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg caggccccg tggcggggg     540 actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
```

```
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggcg gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg ccgcgttgct   1440
ggcgttttc cataggctcc gccccctga cgagcatcac aaaaatcgac gctcaagtca    1500
gaggtggcga aacccgacag gactataaag ataccaggcg tttccccctg gaagctccct   1560
cgtgcgctct cctgttccga ccctgccgct taccggatac ctgtccgcct ttctcccttc   1620
gggaagcgtg gcgctttctc atagctcacg ctgtaggtat ctcagttcgg tgtaggtcgt   1680
tcgctccaag ctgggctgtg tgcacgaacc ccccgttcag cccgaccgct gcgccttatc   1740
cggtaactat cgtcttgagt ccaacccggt aagacacgac ttatcgccac tggcagcagc   1800
cactggtaac aggattagca gagcgaggta tgtaggcggt gctacagagt tcttgaagtg   1860
gtggcctaac tacggctaca ctagaaggac agtatttggt atctgcgctc tgctgaagcc   1920
agttaccttc ggaaaaagag ttggtagctc ttgatccggc aaacaaacca ccgctggtag   1980
cggtggtttt tttgtttgca agcagcagat tacgcgcaga aaaaaaggat ctcaagaaga   2040
tccttttgatc ttttctacgg ggtctgacgc tcagtggaac gaaaactcac gttaagggat   2100
tttggtcatg agattatcaa aaaggatctt cacctagatc cttttaaatt aaaaatgaag   2160
ttttaaatca atctaaagta tatatgagta aacttggtct gacagttacc aatgcttaat   2220
cagtgaggca cctatctcag cgatctgtct atttcgttca tccatagttg cctgactccc   2280
cgtcgtgtag ataactacga tacgggaggg cttaccatct ggccccagtg ctgcaatgat   2340
accgcgagac ccacgctcac cggctccaga tttatcagca ataaaccagc cagccggaag   2400
ggccgagcgc agaagtggtc ctgcaacttt atccgcctcc atccagtcta ttaattgttg   2460
ccgggaagct agagtaagta gttcgccagt taatagtttg cgcaacgttg ttgccattgc   2520
ttcatctaca ctcaaaaccg tacacatagt gtagccagct gtccagtttt cgcacactac   2580
gttagcaact gaacatattt tgtggttgat cagtcaataa gctgtccata tggacgagaa   2640
agaggttcgc gcgatgattc agcgcaaaga accgaacga aaaatgcagg tcatcaagca    2700
ggcgtccgtg gatctgtcac actcctggca gaccattcag aacgcgcacg actccacgac   2760
tgtcgcaatg gagctacgag aagccgggct caacgcgaa ttctggctac aagctctcgc    2820
ggacatcaca tctgttgtgg gaactgcctc tgagctgcgc aaatctattt cccgttttct   2880
cgttgacgag cttgacgtca gcagccgaac cgttgccacc gttgcagatg tttcaccgtc   2940
gaccatcagt acttggcgtg gtgagcatga gtcatcgtaa aaacatcctc tgacctgcta   3000
tggccccaat gatcacctat taccaaggcg gcggcttcgc cgccgctgcc agcaggctcc   3060
cccacctacg cgctccgctt cgctcgcgct tcggtgctcc gcccgcaggc ccaggagcga   3120
```

-continued

```
gtttgcgcct cgtttagtcc atctaagggg ttcctagctg gcttgaggtc gcaacgcatc      3180
ctgaagtcga tcgaggagca ggaacgcatc atctcgatcc agcgtggttt cttgaccata      3240
aatcgagagg tacacgccca tgacaacgcc atcgacgtct accgaagctg gattcgctgc      3300
gatgccaaga ggacgttcgt tgatgctcat gtgatgggtt tacctgcaaa aatagtcagc      3360
agccaaatcg gaggcggcgg cttcgccgcc gctgccagca ggctccccca cctacgcgct      3420
ccgcttcgct cgcgcttcgg tgctccgccc gcaggcccag gagcgagttt gcgcctcgtt      3480
tagtccatct aaggggttcc tagctggctt gaggtcgcaa cgcatcctga agtcgatcga      3540
ggagcaggaa cgcatcatct cgatccagcg tggtttcttg accataaatc gagaggtaca      3600
cgcccatgac aacgccatcg acgtctaccg aagctggatt cgctgcgatg ccaagaggac      3660
gttcgttgat gctcatgtga tgggtttacc tgcaaaaata gtcagcagcc aaatcggccg      3720
gccttttttct atctgcccgg tcagcccccc gagaccaacc atgaaacagg ccgtctctct      3780
gtcaaggcca agccgctacg cggtgctatc gcagccctga cagagagaca cccagcttca      3840
gagcggcaag tatcgggggg atgccctcaa gtgtggttca tgcgggtgaa agttgttgct      3900
cagcaacgct tttcacttgc gaaccgatat tatcgggggc cgcacatccg ctgcgggcaa      3960
tcgataatgc aagtgatcac gaagattttc ccaagtcgcg ccagcttcga cgagtccgag      4020
gatctcgccg aagacgtaag gcgcacaagt ccgaatcatc atccacgatc gcgccggaat      4080
gatcgcaacc atgaccgggg cagattcttc ctgctcaacg atctgagcat ctgttagttc      4140
tgccccaaga ccagctcggg cacgcaatcc acgggaccac gcgattgccc gacgtcccat      4200
cgaaccaaac tcaaattctc gccacagttc aacgcttgt ggatccccgc ccactgcatc       4260
aacagcgatt tcccagggtg cacggttgcc atgtcgacca ctttttccgt cgccactacc      4320
aacctccata ccaacgccag atgcaatttt cgtcagatac gcagcgagaa cttgatcagc      4380
ttcaccgccg atctttcgta catcgagacc acccgaatta cgtagtggcg cagcaaatcc      4440
cagagatacg agtttggaag tccaccgatc gaacatcgca tccgagaagg attcgaggat      4500
gttctcactc acgtcaccac tgaacatgag tagcgcgtga acgtggacgt gccagccgtt      4560
ttttccgtga gtgatttcaa cagcgcgcac gtatccgtcg cagccgtaca tttcacgttc      4620
cgtacgccaa cgacgaccgt tggtcgcagc tttccaggct gccgaaagtc cagtccatag      4680
gtcgtggagc cgctgaccag ctgtatggcg catggtcatc gtcaccatcg caacagatcc      4740
agtcccgagt tgatgagcaa caacttgaga aatttcgtct gcacgatgtg caccgacttt      4800
tcccgcacag caggggcaga tccagccctt tccgcaggaa cgaaggcctc cgaatccaga      4860
acctttcgga ccgttgacaa tggtcacacc gttcacgcca gaaatcggcc ggccacaggc      4920
gttaaatgtt tctgacgtgg tgatttgttg aagtttgggt cgcagttcgt gccggatgcc      4980
gcgcttatcg gacgacacga ggacgggagg ccggtctttg ccggaaaggt gttcagcact      5040
tacgctggtc ataacgagcg gggtcctagt caagtaggag cctcgaaggc ggcggcaggg      5100
tggtccaaca cccttcgtcg ccgctcgtat tttcggagta atccagcta gttcagctcg       5160
gatactccac ttcgaggttc atcgattatt tggtttttat ccacttaacc agcagaaaca      5220
gcgtttatcg ctgatctgct ggtcagtgcg gcgtgtcggg ggagtcgcta gtccgcggcg      5280
agtccccatg cttcgagaac accgaccttc tcttctgggg ttctgcttgt cttcaccagt      5340
gcatcgaaca gacctcggta ttcacccaag tgttcaatat cgaatccggc ttccctggcg      5400
taatcagggg tgtagtagca gcacatcgca gccagaatct cggacgattc ggcgcgttca      5460
```

-continued

```
ccagcatgaa tccaaccata aacgtcatgc ccaccccata gatcaggccc tcgatgatcg   5520
taaatgccaa cggctagtcg gaggatgaat accgtagctt cgtgcttcac gcatcaaccc   5580
tctgatctgc tgcactcaga attgcatgac ctcccgaatg actgcataac tcgtcgtaga   5640
cctgagcaac gaacgaaggc cgatcagcat tgtccatgaa gagttggacg aacttcggcc   5700
ggacgaggcc aatccacggc gcagtcaaag tttcaaaatc atgtgcctcg aggtgctcat   5760
gcattgcaac cgcccatgcg gcccctcgag cggcgcacca gtctcgttca actccctcgc   5820
tgtccgaaat gtcgtattta aggcccagtg atcgtccaac ttcggcagct gcgtcactgg   5880
cacgtttcca atcgtcaccg cgtaagtcgt tgagctttcc gagttcatcg cctagaagca   5940
gctcagacat tgcaaaaacg gtcatcgaac tgacccatcg tggaccgact agtgcaccaa   6000
ggtcgtcgtc ggtgatctgc atgccgcgaa gttcgtcgac gacagcttgg ccttccaaac   6060
ctactctggc cctgagtatt tcagttatta cgagatgatc gttcggccag cctgatttga   6120
tccggagtgc agtcgttacg actcgttccg tgggcaggtt tcggcgtgag gcgagttttt   6180
ctcctgcctc atgtgcaacc ttctcaaatt gctgtcgaat gtaggtgttt accgggattg   6240 cgtcgtcgg gtagccgatc aaggtgtgtc ctcctgtgtg ttcggttgtc agcctatgtc   6300
gccgagatgt gggtattccg aggcgattgt cattcgttgt gctcggtcga tgttcagtgc   6360
ggcttcgtac gcgaggtctg cgttttcgac gtaactcgcg taggtcgagt actcacctac   6420
gcgaaccgtt cggatcattt ggcgccgtag tccgggttgg tcgaagaagc cttgaccagg   6480
gacgaatcct tcgaccagtg cgcactcttc aggtgttgcg ttggggtgca gcattttgac   6540
agattcaggt tcgtctacgc ggagagtcat tttcaccgcg aagttcgagc gggcgtttcc   6600
acccacgatg gaagcttccg cacgttgagc caagagcaac attctgatgc ctgctttggc   6660
agactgagca gcgatctgtc gaacaagcga tgtgatgcgg ggtgcgtatc tgtctgctgg   6720
tttcagaccg ttggttgcat cgaaatcctg tgcgccctcg atgattccgg gaaattcttc   6780
cagtacgagc aggatgagag gtagtgctgg cgagaacaac gaaattttgt ctatgcgtcg   6840
atcccagaaa cactcgattc gtcggtcaga ttctgctttg acgaactgga gcactcggag   6900
gactttgtca aaatcgttca gcccgagctc gatgttcggt tcagccggtc gtcggtggac   6960
gaatggggct agtaagacgg aagtgggatc gactccgacg acacgcacag cgggattcga   7020
tccagcctgt gcgagcaggt tgtaggtgca ttgagatttt ccggaacggg ttttgccttg   7080
aatgagccag tgagcagcat ctttggctat atcgaccatg acaggttgag ctagttcgtt   7140
ccatccaatc gcaatcggga tcgtgtctgt ttgatccatc aggcgtccgt gcttttgtcg   7200
aacggaagat cctttccttg ctcccaccag ggccgattgt ccccgagtat gccgccggcc   7260
tcttccttca atgtgccggc cgatgagtcc tcgacgtcac tgagccatgc tgcatctcgt   7320
gcttgagaaa tggtgtctgc atcgatcaga agtagctcga cccgacgcgg ctctactttg   7380
gtgaaactgg cacgtagagc accgaaagca tcggctattt tgaccgtctt cgatgtcata   7440
tcttcaccgg tgatccctgt cggaaggtcg aaagcgactg atcgagtcaa tccgtcgtcc   7500
gaaaatttgt agctacgaat gatgggaggc tgcccagagg agttgatcag accaagattg   7560
gccgcagcac ctgcaacttc cggggttcct cgccaccatc gagctgtacg acgtttgcga   7620
cgccgagcct tcgttgcctc tctcaggtag accattgcca caacgcacac cagcagcaca   7680
ctgaccaaaa gccacatctg agcgtcgaag atgtacagca gcagaagcaa cagaaacgta   7740
gaggacagaa tcgggtaatc ggcaattttt gccttgagtt ttgctcgcaa aatttgccag   7800
gtggaacgtc ttttaacctg gtcaccgcgt cgaacggctt cgtagttgct catcggggcc   7860
```

-continued

```
actccacaac gacattcgga ctatctactt cgacttgctc atctacgttc cacaaccacg    7920
attcgactgg aacgagagcg catcccgagg ttccattctg aagattgctt tgcactcgat    7980
cactcatcaa agtctctgga accgtctcag cctctacgcc cttatgtacc gggacagggg    8040
tattcacggt caaatacact gcccgccagc cctcaggcac tggcacgtca ccgcacgcgc    8100
tggtcttcga gtacggcgac gtgatgacct tccatctgg gttagtccac tggatcccat    8160
cggcgctcaa ttccggattc actcggatgt atccaggtat ctctctgcat gcactgacag    8220
atggaacaga acctgtcgga agaggggatc tgcaccaggt caccgttcgt tcagcccatg    8280
agtcccgacg ctcttgcatt ccgctggaaa gcttaatatc ttgcgtgcca caatctggaa    8340
tattacggcc ttttttaaaga ccgtaaagaa aaataagcac aagttttatc cggcctttat    8400
tcacattctt gcccgcctga tgaatgctca tccggaattc cgtatggcaa tgaaagacgg    8460
tgagctggtg atatgggata gtgttcaccc ttgttacacc gttttccatg agcaaactga    8520
aacgttttca tcgctctgga gtgaatacca cgacgatttc cggcagtttc tacacatata    8580
ttcgcaagat gtggcgtgtt acggtgaaaa cctggcctat ttccctaaag ggttattga    8640 gaatatgttt ttcgtctcag ccaatccctg ggtgagtttc accagttttg atttaaacgt    8700
ggccaatatg gacaacttct tcgcccccgt tttcaccatg ggcaaatatt atacgcaagg    8760
cgacaaggtg ctgatgccgc tggcgattca ggttcatcat gccgtttgtg atggcttcca    8820
tgtcggcaga atgcttaatg aattacaaca gtactgcgat gagtggcagg gcggggcgta    8880
atttttttaa ggcagttatt ggtgcccta acgcctggt gctacgcctg aataagtgat    8940
aataagcgga tgaatggcag aaattcgaaa gcaaattcga cccggtcgtc ggttcagggc    9000
agggtcgtta aatagccgct tatgtctatt gctggtttac cggtttattg actaccggaa    9060
gcagtgtgac cgtgtgcttc tcaaatgcct gaggccagtt tgctcaggct ctccccgtgg    9120
aggtaataat tgacgatatg atcatttatt ctgcctccca gagcctgata aaaacggtga    9180
atccgttagc gaggtgccgc cggcttccat tcaggtcgag gtggcccggc tccatgcacc    9240
gcgacgcaac gcggggaggc agacaaggta tagggcggcg cctacaatcc atgccaaccc    9300
gttccatgtg ctcgccgagg cggcataaat cgccgtgacg atcagcggtc cagtgatcga    9360
agttaggctg gtaagagccg cgagcgatcc ttgaagctgt ccctgatggt cgtcatctac    9420
ctgcctggac agcatggcct gcaacgcggg catcccgatg ccgccggaag cgagaagaat    9480
cataatgggg aaggccatcc agcctcgcgt cgcgaacgcc agcaagacgt agcccagcgc    9540
gtcggccgcc atgccggcga taatggcctg cttctcgccg aaacgtttgg tggcgggacc    9600
agtgacgaag gcttgagcga gggcgtgcaa gattccgaat accgcaagcg ac             9652
```

<210> SEQ ID NO 8
<211> LENGTH: 29
<212> TYPE: DNA
<213> ORGANISM: Rhodococcus AN12

<400> SEQUENCE: 8
gtgcgaaaac tggacagctg gctacacta                                       29

<210> SEQ ID NO 9
<211> LENGTH: 19
<212> TYPE: DNA
<213> ORGANISM: Primer

<400> SEQUENCE: 9
gagtttgatc ctggctcag                                                19

<210> SEQ ID NO 10
<211> LENGTH: 16
<212> TYPE: DNA
<213> ORGANISM: Primer

<400> SEQUENCE: 10
taccttgtta cgactt                                                   16

<210> SEQ ID NO 11
<211> LENGTH: 17
<212> TYPE: DNA
<213> ORGANISM: Primer

<400> SEQUENCE: 11
gtgccagcag ymgcggt                                                  17

<210> SEQ ID NO 12
<211> LENGTH: 1424
<212> TYPE: DNA
<213> ORGANISM: Rhodococcus AN12

<400> SEQUENCE: 12
tcgagcggta gagagaagct tgcttctctt gagagcggcg gacgggtgag taatgcctag    60
gaatctgcct ggtagtgggg gataacgttc ggaaacggac gctaataccg catacgtcct   120
acggagaaa gcaggggacc ttcgggcctt gcgctatcag atgagcctag gtcggattag   180
ctagttggtg aggtaatggc tcaccaaggc gacgatccgt aactggtctg agaggatgat   240
cagtcacact ggaactgaga cacggtccag actcctacgg gaggcagcag tggggaatat   300
tggacaatgg gcgaaagcct gatccagcca tgccgcgtgt gtgaagaagg tcttcggatt   360
gtaaagcact ttaagttggg aggaagggca gttacctaat acgtgattgt tttgacgtta   420
ccgacagaat aagcaccggc taactctgtg ccagcagccg cggtaataca gagggtgcaa   480
gcgttaatcg gaattactgg gcgtaaagcg cgcgtaggtg gtttgttaag ttggatgtga   540
aatccccggg ctcaacctgg gaactgcatt caaaactgac tgactagagt atggtagagg   600
gtggtggaat ttcctgtgta gcggtgaaat gcgtagatat aggaaggaac accagtggcg   660
aaggcgacca cctggactga tactgacact gaggtgcgaa agcgtgggga gcaaacagga   720
ttagataccc tggtagtcca cgccgtaaac gatgtcaact agccgttggg agccttgagc   780
tcttagtggc gcagctaacg cattaagttg accgcctggg gagtacggcc gcaaggttaa   840
aactcaaatg aattgacggg gcccgcaca agcggtggag catgtggttt aattcgaagc   900
aacgcgaaga accttaccag gccttgacat ccaatgaact ttctagagat agattggtgc   960
cttcgggaac attgagacag gtgctgcatg gctgtcgtca gctcgtgtcg tgagatgttg  1020
ggttaagtcc cgtaacgagc gcaacccttg tccttagtta ccagcacgta atggtgggca  1080
ctctaaggag actgccggtg acaaaccgga ggaaggtggg gatgacgtca agtcatcatg  1140
gcccttacgg cctgggctac acacgtgcta caatggtcgg tacagagggt tgccaagccg  1200
cgaggtggag ctaatcccag aaaaccgatc gtagtccgga tcgcagtctg caactcgact  1260
gcgtgaagtc ggaatcgcta gtaatcgcga atcagaatgt cgcggtgaat acgttcccgg  1320
gccttgtaca caccgcccgt cacaccatgg gagtgggttg caccagaagt agctagtcta  1380
accctcggga ggacggttac cacggtgtga ttcatgactg ggt                    1424

<210> SEQ ID NO 13
<211> LENGTH: 17
<212> TYPE: DNA
<213> ORGANISM: Primer

<400> SEQUENCE: 13
gtaaaacgac ggccagt                                                    17

<210> SEQ ID NO 14
<211> LENGTH: 24
<212> TYPE: DNA
<213> ORGANISM: Primer

<400> SEQUENCE: 14
agcggataac aatttcacac agga                                            24

<210> SEQ ID NO 15
<211> LENGTH: 722
<212> TYPE: DNA
<213> ORGANISM: Rhodococcus AN12

<400> SEQUENCE: 15 aagcttttcca gcggaatgca agagcgtcgg gactcatggg ctgaacgaac ggtgacctgg    60
tgcagatccc ctcttccgac aggttctgtt ccatctgtca gtgcatgcag agagatacct    120
ggatacatcc gagtgaatcc ggaattgagc gccgatggga tccagtggac taacccagat    180
ggaaaggtca tcacgtcgcc gtactcgaag accagcgcgt gcggtgacgt gccagtgcct    240
gagggctggc gggcagtgta tttgaccgtg aatacccctg tcccggtaca taagggcgta    300
gaggctgaga cggttccaga gactttgatg agtgatcgag tgcaaagcaa tcttcagaat    360
ggaacctcgg gatgcgctct cgttccagtc gaatcgtggt tgtggaacgt agatgagcaa    420
gtcgaagtag atagtccgaa tgtcgttgtg gagtggcccc gatgagcaac tacgaagccg    480
ttcgacgcgt tgaccaggtt aaaagacgtt ccacctggca aattttgcga gcaaaactca    540
aggcaaaaat tgccgattac ccgattctgt cctctacgtt tctgttgctt ctgctgctgt    600
acatcttcga cgctcagatg tggcttttgg tcagtgtgct gctggtgtgc gttgtggcaa    660
tggtctacct gagagaggca acgaaggctc ggcgtcgcaa acgtcgtaca gctcgatggt    720
gg                                                                    722

<210> SEQ ID NO 16
<211> LENGTH: 523
<212> TYPE: DNA
<213> ORGANISM: Rhodococcus AN12

<400> SEQUENCE: 16
aagcttccgc acgttgagcc aagagcaaca ttctgatgcc tgctttggca gactgagcag    60
cgatctgtcg aacaagcgat gtgatgcggg gtgcgtatct gtctgctggt ttcagaccgt    120
tggttgcatc gaaatcctgt gcgccctcga tgattccggg aaattcttcc agtacgagca    180
ggatgagagg tagtgctggc gagaacaacg aaattttgtc tatgcgtcga tcccagaaac    240
actcgattcg tcggtcagat tctgctttga cgaactggag cactcggagg actttgtcaa    300
aatcgttcag cccgagctcg atgttcggtt casccggtcg tcggtggacg aatgggcta    360 gtaagacgga agtgggatcg actccgacga cacgcacagc gggattcgat ccagcctgtg    420
cgagcaggtt gtaggtgcat tgagattttc cggaacgggt tttgccttga atgagccagt    480
gagcagcatc tttggctata tcgaccatga caggttgagc tag                      523

-continued

```
<210> SEQ ID NO 17
<211> LENGTH: 606
<212> TYPE: DNA
<213> ORGANISM: Rhodococcus AN12

<400> SEQUENCE: 17
aagcttccat cgtgggtgga acgcccgct cgaacttcgc ggtgaaaatg actctccgcg      60
tagacgaacc tgaatctgtc aaaatgctgc accccaacgc aacacctgaa gagtgcgcac   120
tggtcgaagg attcgtccct ggtcaaggct tcttcgacca acccggacta cggcgccaaa   180
tgatccgaac ggttcgcgta ggtgagtact cgacctacgc gagttacgtc gaaaacgcag   240
acctcgcgta cgaagccgca ctgaacatcg accgagcaca acgaatgaca atcgcctcgg   300
aatacccaca tctcggcgac ataggctgac aaccgaacac acaggaggac acaccttgat   360
cggctacccg acagacgcaa tcccggtaaa cacctacatt cgacagcaat ttgagaaggt   420
tgcacatgag gcaggagaaa aactcgcctc acgccgaaac ctgcccacgg aacgagtcgt   480
aacgactgca ctccggatca aatcaggctg ccgaacgat catctcgtaa taactgaaat    540
actcagggcc agagtaggtt tggaaggcca agctgtcgtc gacgaacttc gcggcatgca   600
gatcac                                                             606

<210> SEQ ID NO 18
<211> LENGTH: 30
<212> TYPE: DNA
<213> ORGANISM: Primer

<400> SEQUENCE: 18
actttattgt catagtttag atctattttg                                     30

<210> SEQ ID NO 19
<211> LENGTH: 20
<212> TYPE: DNA
<213> ORGANISM: Primer

<400> SEQUENCE: 19
acttgcgaac cgatattatc                                                20

<210> SEQ ID NO 20
<211> LENGTH: 20
<212> TYPE: DNA
<213> ORGANISM: Primer

<400> SEQUENCE: 20
ttatgaccag cgtaagtgct                                                20

<210> SEQ ID NO 21
<211> LENGTH: 459
<212> TYPE: PRT
<213> ORGANISM: Arcanobacterium pyogenes

<400> SEQUENCE: 21

Met Asn Arg Leu Ser Glu Arg Thr Ala Leu Ser Leu Pro Ala Arg Gln
 1               5                  10                  15

Ile Gln Lys Val Ile Pro Ala Ala Gly Gly Arg Ser Leu Lys Ser Phe
            20                  25                  30

Glu Gly Met Thr Ala Thr Trp Ser Ala Arg Gly Gly Ala Ser Ser Asp
        35                  40                  45

Glu Arg Ser Arg Asp Lys Arg Ser Gln Ile Pro Ser Asn Arg Arg Glu
    50                  55                  60
```

```
Gly Arg Ser Ala Thr His Pro Leu Gly Asn Thr Val Leu Thr Phe Pro
 65                  70                  75                  80

Val Ser Asn Glu Ser Lys Lys Thr Ala Lys Ser Arg Arg Ser Glu Arg
                 85                  90                  95

Tyr Glu Leu Arg Asp Gly Leu Ala Glu Ile Ser Thr Ile Glu Ser Val
            100                 105                 110

Arg Lys Cys Gly Arg Val Pro Val Ala Pro Leu Val Ser Leu Arg Ala
            115                 120                 125

Lys Ser Asp Gly Lys Gly Ala Gly Tyr Gly Gly Leu His Thr Cys Gly
130                 135                 140

Ser Val Trp Ala Cys Pro Val Cys Ser Ala Lys Ile Ala Ala Arg Arg
145                 150                 155                 160

Lys Thr Asp Leu Gln Gln Val Val Asp His Ala Val Lys His Gly Met
                165                 170                 175

Thr Val Ser Met Leu Thr Leu Thr Gln Arg His His Lys Gly Gln Gly
            180                 185                 190

Leu Lys His Leu Trp Asp Ala Leu Ser Thr Ala Trp Asn Arg Val Thr
        195                 200                 205

Ser Gly Arg Arg Trp Ile Glu Phe Lys Glu Gln Phe Gly Leu Val Gly
    210                 215                 220

Tyr Val Arg Ala Asn Glu Ile Thr His Gly Lys His Gly Trp His Val
225                 230                 235                 240

His Ser His Val Leu Ile Ile Ser Glu Lys Asp Pro Leu Thr Ser Thr
                245                 250                 255

Phe Val Tyr Gln Arg Lys Gln Gly Arg Arg Leu Pro Tyr Pro Pro
            260                 265                 270

Glu Ile Tyr Met Ser Ser Asp Phe Ile Ala Glu Arg Trp Glu Ala Gly
        275                 280                 285

Leu Ala Lys His Gly Val Asp Phe Leu Arg Asp Ser Gly Gly Leu Asp
    290                 295                 300

Trp Thr Val Ala Lys Asp Ala Arg Ala Ile Gly Asn Tyr Val Ser Lys
305                 310                 315                 320

Met Gln Thr Ser Thr Asp Ala Ile Ser Ser Glu Val Thr Leu Gly Gly
                325                 330                 335

Phe Lys Lys Ala Arg Asn Gly Asn Arg Thr Pro Phe Gln Ile Leu Ala
            340                 345                 350

Asp Ile Leu Ser Leu Gly Asp Val Asp Asp Leu Lys Leu Trp Lys Glu
        355                 360                 365

Tyr Glu Lys Ala Ser Phe Gly Arg Arg Ala Leu Thr Trp Ser Lys Gly
    370                 375                 380

Leu Arg Asp Trp Ala Asn Leu Gly Val Glu Gln Ser Asp Glu Glu Ile
385                 390                 395                 400

Ala Ser Glu Glu Ile Gly Asp Glu Ala Ile Ala Leu Phe Thr His Asp
                405                 410                 415

Ala Trp Arg Gln Val Arg Arg Phe Gly Ala Ala Glu Leu Leu Asp Val
            420                 425                 430

Thr Glu Ser Gly Gly Arg Ala Ala Tyr Arg Trp Leu Asp Phe Arg
        435                 440                 445

Glu Ile Asp Trp Ser Leu Pro Pro Lys Ile Glu
450                 455

<210> SEQ ID NO 22
<211> LENGTH: 456
```

```
<212> TYPE: PRT
<213> ORGANISM: Streptomyces lividans

<400> SEQUENCE: 22
```

Met Asp Pro Ala Ser Gly Val Ile Val Ala Gln Thr Ala Gly Thr
1               5                   10                  15

Ser Val Val Leu Gly Leu Met Arg Cys Gly Arg Ile Trp Leu Cys Pro
            20                  25                  30

Val Cys Ala Ala Thr Ile Arg His Lys Arg Ala Glu Ile Thr Ala
            35                  40                  45

Ala Val Val Glu Trp Ile Lys Arg Gly Thr Ala Tyr Leu Val Thr
    50                  55                  60

Phe Thr Ala Arg His Gly His Thr Asp Arg Leu Ala Asp Leu Met Asp
65                  70                  75                  80

Ala Leu Gln Gly Thr Arg Lys Thr Pro Asp Ser Pro Arg Arg Pro Gly
                85                  90                  95

Ala Tyr Gln Arg Leu Ile Thr Gly Gly Thr Trp Ala Gly Arg Arg Ala
            100                 105                 110

Lys Asp Gly His Arg Ala Ala Asp Arg Glu Gly Ile Arg Asp Arg Ile
            115                 120                 125

Gly Tyr Val Gly Met Ile Arg Ala Thr Glu Val Thr Val Gly Gln Ile
130                 135                 140

Asn Gly Trp His Pro His Ile His Ala Ile Val Leu Val Gly Gly Arg
145                 150                 155                 160

Thr Glu Gly Glu Arg Ser Ala Lys Gln Ile Val Ala Thr Phe Glu Pro
                165                 170                 175

Thr Gly Ala Ala Leu Asp Glu Trp Gln Gly His Trp Arg Ser Val Trp
            180                 185                 190

Thr Ala Ala Leu Arg Lys Val Asn Pro Ala Phe Thr Pro Asp Asp Arg
            195                 200                 205

His Gly Val Asp Phe Lys Arg Leu Glu Thr Glu Arg Asp Ala Asn Asp
            210                 215                 220

Leu Ala Glu Tyr Ile Ala Lys Thr Gln Asp Gly Lys Ala Pro Ala Leu
225                 230                 235                 240

Glu Leu Ala Arg Ala Asp Leu Lys Thr Ala Thr Gly Gly Asn Val Ala
                245                 250                 255

Pro Phe Glu Leu Leu Gly Arg Ile Gly Asp Leu Thr Gly Gly Met Thr
            260                 265                 270

Glu Asp Asp Ala Ala Gly Val Gly Ser Leu Glu Trp Asn Leu Ser Arg
            275                 280                 285

Trp His Glu Tyr Glu Arg Ala Thr Arg Gly Arg Arg Ala Ile Glu Trp
290                 295                 300

Thr Arg Tyr Leu Arg Gln Met Leu Gly Leu Asp Gly Asp Thr Glu
305                 310                 315                 320

Ala Asp Asp Leu Asp Leu Leu Ala Ala Asp Ala Asp Gly Gly Glu
                325                 330                 335

Leu Arg Ala Gly Val Ala Val Thr Glu Asp Gly Trp His Ala Val Thr
            340                 345                 350

Arg Arg Ala Leu Asp Leu Glu Ala Thr Arg Ala Ala Glu Gly Lys Asp
            355                 360                 365

Gly Asn Glu Asp Pro Ala Ala Val Gly Glu Arg Val Arg Glu Val Leu
            370                 375                 380

Ala Leu Ala Asp Ala Ala Asp Thr Val Val Val Leu Thr Ala Gly Glu
385                 390                 395                 400

```
Val Ala Glu Ala Tyr Ala Asp Met Leu Ala Leu Ala Gln Arg Arg
            405                 410                 415

Glu Glu Ala Thr Ala Arg Arg Arg Glu Gln Asp Asp Gln Asp
            420                 425                 430

Asp Asp Ala Asp Arg Gln Glu Arg Ala Ala Arg His Ile Ala Arg
            435                 440                 445

Leu Ala Ser Gly Pro Thr Ser His
            450                 455

<210> SEQ ID NO 23
<211> LENGTH: 528
<212> TYPE: PRT
<213> ORGANISM: Streptomyces phaeochromogenes

<400> SEQUENCE: 23

Met Leu Asn Arg Val Ser Gly Ile Asp Ala Cys Gly Cys Gly Arg
1               5                   10                  15

Arg Val Leu Asp Pro Asp Thr Gly Val Ile Tyr Ala Lys Ser Ser Arg
                20                  25                  30

Gly Tyr Val Val Thr Ile Gly Leu Val Arg Cys Gly Arg Ile Trp Phe
            35                  40                  45

Cys Pro Glu Cys Ser Ser Ala Ile Arg Arg Gly Arg Thr Glu Glu Ile
        50                  55                  60

Lys Thr Gly Ala Leu Arg His Leu Ala Ala Gly Gly Thr Leu Ala Val
65                  70                  75                  80

Val Val Leu Thr Ala Arg His Asn Gln Thr Thr Asp Leu Asp Ser Leu
                85                  90                  95

Val Ala Ala Leu Trp Gly Gly Pro Leu Leu Asp Asp Lys Gly Ala Pro
            100                 105                 110

Val Leu Asp Arg Ser Gly Lys Pro Arg Arg Ala Pro Gly Ala Tyr Gln
            115                 120                 125

Arg Met Leu Thr Ala Pro Ala Phe Tyr Gly Arg Pro Glu Ala Arg Arg
    130                 135                 140

Thr Arg Lys Asp Gly Thr Gln Tyr Val Arg Pro Ala Glu Asp Gly Ile
145                 150                 155                 160

Arg His Arg Ile Gly Tyr Ile Gly Met Val Arg Ala Ala Glu Val Thr
                165                 170                 175

Arg Ser Lys Lys Asn Gly Tyr His Pro His Leu Asn Leu Leu Val Phe
            180                 185                 190

Leu Gly Gly Glu Leu Ser Gly Thr Pro Ala Lys Gly Asp Val Val Gly
        195                 200                 205

His Phe Glu Pro Ser Glu Thr Asp Leu Gly Asp Trp Glu Asp Trp Leu
    210                 215                 220

Arg Glu Met Trp Ala Gly Ala Leu Lys Arg Ala Asp Pro Lys Phe Glu
225                 230                 235                 240

Pro Ser Thr Asp Cys Asp Thr Pro Gly Cys Lys Cys Lys Gly Lys Gly
                245                 250                 255

His Gly Val Met Val Ser Ile Val Arg Ser Ala Asp Val Ala Leu
            260                 265                 270

Ile Glu Tyr Leu Thr Lys Asn Gln Asp Gly Lys Arg Glu Arg Pro Asp
        275                 280                 285

Ser Val Asp Gln Asp Leu Glu Ala Ala Gly Ala Ala Met Glu Thr
    290                 295                 300

Ala Arg Leu Asp Ser Lys Thr Gly Arg Gly Arg Lys Ser Met Thr Pro
```

-continued

```
                305                 310                 315                 320

Phe Gln Ile Leu Tyr Arg Leu Trp Asp Ile Glu Val Ala Gly Leu Asp
                325                 330                 335

Pro Asp Met Ala Glu Gly Tyr Gly Thr Pro Lys Gln Leu Arg Ala Trp
            340                 345                 350

Trp Ala Gln Tyr Glu Glu Ala Leu Ala Gly Arg Arg Ala Ile Glu Trp
        355                 360                 365

Thr Arg Gly Leu Arg Arg His Val Asp Leu Asp Gly Asp Asp Asp Glu
    370                 375                 380

Glu Thr Asp Leu Gln Tyr Val Tyr Glu Pro Glu Ala Ala Pro Leu Asp
385                 390                 395                 400

Gly Gly Val Val Leu Thr Ser Asp Ala Met Arg Leu Val Val Gly Ala
                405                 410                 415

Asp Ala Glu Leu Asp Leu Asp Val Val Arg Ala Glu Ala Tyr Tyr
            420                 425                 430

Ser Ala Val Asp Val Val Thr Gly Leu Gly Gly Arg Ala Asp His Val
        435                 440                 445

Arg Val Ala Thr Ala Glu Glu Leu Ala Glu Val Gln Glu Val Leu Phe
    450                 455                 460

Ala Arg Thr Gln Glu Arg Ala Glu Glu Ser Arg Arg Gln Arg Ile
465                 470                 475                 480

Ala Glu His Glu Ala Glu Gln Ala Ala His Arg Lys Arg Gln Glu
                485                 490                 495

Leu Ala Arg Cys Leu Gly Leu Leu Val Arg Gln Arg Gly Gly Thr Gln
            500                 505                 510

Asp Asp Ser Ala Ala Asp Asn Phe Val Ala His Ile His Ala Asn Arg
        515                 520                 525

<210> SEQ ID NO 24
<211> LENGTH: 451
<212> TYPE: PRT
<213> ORGANISM: Streptomyces nigirifaciens

<400> SEQUENCE: 24

Met Asp Pro Ala Ser Gly Val Ile Val Ala Gln Thr Ala Ala Gly Thr
1               5                   10                  15

Ser Val Val Leu Gly Leu Met Arg Cys Gly Arg Ile Trp Leu Cys Pro
            20                  25                  30

Val Cys Ala Ala Thr Ile Arg His Lys Arg Ala Glu Glu Ile Thr Ala
        35                  40                  45

Ala Val Val Glu Trp Ile Lys Arg Gly Gly Thr Ala Tyr Leu Val Thr
    50                  55                  60

Phe Thr Ala Arg His Gly His Thr Asp Arg Leu Ala Asp Leu Met Asp
65                  70                  75                  80

Ala Leu Gln Gly Thr Arg Lys Thr Ala Asp Ala Pro Arg Arg Pro Gly
                85                  90                  95

Ala Tyr Gln Arg Leu Ile Thr Gly Gly Thr Trp Ala Arg Arg Ala
            100                 105                 110

Lys Asp Gly His Arg Ala Ala Asp Arg Glu Gly Ile Arg Asp Arg Ile
        115                 120                 125

Gly Tyr Val Gly Met Ile Arg Ala Thr Glu Val Thr Val Gly Gln Ile
    130                 135                 140

Asn Gly Trp His Pro His Ile His Ala Ile Val Leu Val Gly Gly Arg
145                 150                 155                 160
```

-continued

```
Thr Glu Gly Glu Arg Ser Ala Lys Gln Ile Val Gly Thr Phe Glu Pro
                165                 170                 175

Ser Glu Ala Ala Leu Asp Glu Trp Gln Gly Gln Trp Arg Ala Val Trp
            180                 185                 190

Thr Ala Ala Leu Arg Lys Val Asn Pro Gln Phe Thr Pro Asp Asp Arg
        195                 200                 205

His Gly Val Asp Phe Lys Arg Leu Glu Thr Glu Arg Asp Ala Asn Asp
    210                 215                 220

Leu Ala Glu Tyr Ile Ala Lys Thr Gln Asp Gly Lys Ala Pro Ala Leu
225                 230                 235                 240

Glu Leu Ala Arg Ala Asp Leu Lys Thr Ala Asn Gly Gly Asn Val Ala
                245                 250                 255

Pro Phe Glu Leu Leu Gly Arg Ile Gly Asp Leu Thr Gly Gly Met Thr
            260                 265                 270

Glu Asp Asp Ala Ala Gly Val Gly Ser Leu Glu Trp Asn Leu Ala Arg
        275                 280                 285

Trp His Glu Tyr Glu Arg Ala Thr Lys Gly Arg Arg Ala Ile Glu Trp
    290                 295                 300

Thr Arg Tyr Leu Arg Gln Met Leu Gly Leu Asp Gly Gly Asp Thr Glu
305                 310                 315                 320

Ala Asp Asp Leu Asp Leu Leu Ala Ala Asp Ala Asp Gly Gly Glu
                325                 330                 335

Leu Arg Ala Gly Val Ala Val Thr Glu Asp Gly Trp His Ala Val Thr
            340                 345                 350

Arg Arg Ala Leu Asp Leu Ala Ala Thr Gln Ala Ala Glu Gly Thr Asp
        355                 360                 365

Gly Asn Thr Asp Pro Ala Ala Met Gly Glu Arg Val Arg Glu Val Leu
    370                 375                 380

Ala His Ala Asp Ala Ala Asp Ala Val Val Leu Thr Ser Gly Glu
385                 390                 395                 400

Val Ala Glu Ala Tyr Ala Asp Met Leu Ala Ala Leu Ala Leu Arg Arg
                405                 410                 415

Glu Glu Ala Ala Ala Arg Arg Arg Arg Glu Gln Asp Asp Gln Asp
            420                 425                 430

Asp Asp Ala Asp Asp Arg Gln Glu Arg Ala Ala Arg His Ile Ala Arg
        435                 440                 445

Leu Arg Asn
    450

<210> SEQ ID NO 25
<211> LENGTH: 30
<212> TYPE: DNA
<213> ORGANISM: Streptomyces lividans

<400> SEQUENCE: 25
gaggcaaaag cgaacaccct tgggaaagaaa                                    30

<210> SEQ ID NO 26
<211> LENGTH: 30
<212> TYPE: DNA
<213> ORGANISM: Streptomyces phaeochromogenes

<400> SEQUENCE: 26
ctggcaaaaa gggacgccta ggtaaaggtt                                     30

<210> SEQ ID NO 27
```

-continued

```
<211> LENGTH: 31
<212> TYPE: DNA
<213> ORGANISM: Streptomyces nigirifaciens

<400> SEQUENCE: 27
gacccaaaac tgtcgcgcct tgggaaagaa a                              31

<210> SEQ ID NO 28
<211> LENGTH: 20
<212> TYPE: DNA
<213> ORGANISM: Primer

<400> SEQUENCE: 28
atttcgttga acggctcgcc                                           20

<210> SEQ ID NO 29
<211> LENGTH: 20
<212> TYPE: DNA
<213> ORGANISM: Primer

<400> SEQUENCE: 29
cggcaatccg acctctacca                                           20

<210> SEQ ID NO 30
<211> LENGTH: 20
<212> TYPE: DNA
<213> ORGANISM: Primer

<400> SEQUENCE: 30
tgagacgagc cgtcagcctt                                           20
```